United States Patent
Penning et al.

(10) Patent No.: US 11,459,295 B2
(45) Date of Patent: Oct. 4, 2022

(54) 2-BETA-NAPHTHYL-ACETIC ACID ANALOGS AS AKR1C3 INHIBITORS AND METHODS OF USING SAME

(71) Applicants: THE TRUSTEES OF THE UNIVERSITY OF PENNSYLVANIA, Philadelphia, PA (US); VANDERBILT UNIVERSITY, Nashville, TN (US)

(72) Inventors: Trevor M. Penning, Springfield, PA (US); Adegoke Adeniji, Richmond Hill, GA (US); Lawrence J. Marnett, Nashville, TN (US)

(73) Assignees: THE TRUSTEES OF THE UNIVERSITY OF PENNSYLVANIA, Philadelphia, PA (US); VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 15/769,565

(22) PCT Filed: Oct. 21, 2016

(86) PCT No.: PCT/US2016/058075
§ 371 (c)(1),
(2) Date: Apr. 19, 2018

(87) PCT Pub. No.: WO2017/070448
PCT Pub. Date: Apr. 27, 2017

(65) Prior Publication Data
US 2018/0305305 A1   Oct. 25, 2018

Related U.S. Application Data

(60) Provisional application No. 62/244,934, filed on Oct. 22, 2015.

(51) Int. Cl.
| | | |
|---|---|---|
| *A61K 31/405* | (2006.01) |
| *A61K 31/4166* | (2006.01) |
| *A61K 31/506* | (2006.01) |
| *A61K 31/52* | (2006.01) |
| *A61K 31/573* | (2006.01) |
| *A61K 45/06* | (2006.01) |
| *A61P 35/00* | (2006.01) |
| *C07C 57/40* | (2006.01) |
| *C07C 311/51* | (2006.01) |
| *C07C 317/44* | (2006.01) |
| *C07C 323/62* | (2006.01) |
| *C07C 59/64* | (2006.01) |
| *A61K 31/192* | (2006.01) |
| *A61K 31/131* | (2006.01) |
| *A61K 31/16* | (2006.01) |
| *A61K 31/337* | (2006.01) |

(52) U.S. Cl.
CPC .......... *C07C 311/51* (2013.01); *A61K 31/192* (2013.01); *A61K 45/06* (2013.01); *A61P 35/00* (2018.01); *C07C 57/40* (2013.01); *C07C 59/64* (2013.01); *C07C 317/44* (2013.01); *C07C 323/62* (2013.01); *A61K 31/131* (2013.01); *A61K 31/16* (2013.01); *A61K 31/337* (2013.01); *A61K 31/405* (2013.01); *A61K 31/4166* (2013.01); *A61K 31/506* (2013.01); *A61K 31/52* (2013.01); *A61K 31/573* (2013.01); *A61K 2300/00* (2013.01)

(58) Field of Classification Search
CPC ...... C07C 57/40; C07C 245/18; C07C 271/22
See application file for complete search history.

(56) References Cited

U.S. PATENT DOCUMENTS

| | | | | |
|---|---|---|---|---|
| 3,904,682 A | | 9/1975 | Fried et al. | |
| 4,420,639 A | * | 12/1983 | Lake | C07C 43/23 568/328 |
| 4,919,803 A | * | 4/1990 | Doyle | B01D 15/3833 210/198.2 |
| 5,256,293 A | * | 10/1993 | Pirkle | C07D 307/92 210/656 |
| 2007/0276042 A1 | * | 11/2007 | Gant | A61P 43/00 562/466 |
| 2010/0120727 A1 | * | 5/2010 | Xu | A61K 31/195 514/165 |
| 2013/0219528 A1 | | 8/2013 | Borgström et al. | |
| 2014/0107085 A1 | | 4/2014 | Penning et al. | |

FOREIGN PATENT DOCUMENTS

| | | | | | |
|---|---|---|---|---|---|
| BR | PI8201004 | * | 10/1983 | ............. | C07C 31/02 |
| CA | 1049039 A1 | * | 2/1979 | ............. | C07C 31/14 |
| ES | 2023606 | * | 1/1992 | ............. | C07C 59/64 |

OTHER PUBLICATIONS

PubChem CID 20335074 (Create Date: Dec. 5, 2007) (Year: 2007).*
Duggan et al. "Molecular Basis for Cyclooxygenase Inhibition by the Non-steroidal Anti-inflammatory Drug Naproxen" J. Biol. Chem. 2010, 285, 34950-34959. (Year: 2010).*
Xin et al. "Enzymatic resolution of (R, S)-Naproxen in water-saturated ionic liquid" Biocat. Biotransform. 2005, 23, 353-361. (Year: 2005).*
Duh et al. "Enantioselective Synthesis of Naproxen" J. Chin. Chem. Soc. 1992, 39, 465-469. (Year: 1992).*
Harrison et al. "Nonsteroidal Antiinflammatory Agents. I. 6-Substituted 2-Naphthylacetic Acids." J. Med. Chem. 1970, 13, 203-205. (Year: 1970).*
Honda et al. "A General Synthetic Method of Chiral 2-Arylalkanoic Esters via Thermal 1,2-Rearrangment." Bull. Chem. Soc. Jpn. 1987, 60, 1027-1036. (Year: 1987).*

(Continued)

*Primary Examiner* — Amanda L. Aguirre
(74) *Attorney, Agent, or Firm* — Saul Ewing Arnstein & Lehr LLP; Domingos J. Silva

(57) ABSTRACT

The invention includes 2-β-naphthyl-acetic acid derivatives, which are selective AKR1C3 inhibitors. In certain embodiments, the compounds of the invention are (R)-naproxen analogs. The invention further includes methods of treating cancer, such as prostate cancer and/or castration-resistant prostate cancer, using at least one compound of the invention.

17 Claims, 15 Drawing Sheets

(56) References Cited

OTHER PUBLICATIONS

Chemical Abstract Service, STN Database, Registry No. 1630429-92-3 [Entered STN: Oct. 28, 2014], (Year: 2014).*
Chemical Abstract Service, STN Database, Registry No. 1630502-70-3 [Entered STN: Oct. 28, 2014], (Year: 2014).*
Chemical Abstract Service (STN Database) Registry No. 1443679-69-3 [Entered STN: Jul. 11, 2013], (Year: 2013).*
International Search Report and Written Opinion for PCT International Application No. PCT/US2016/058075 dated Jan. 17, 2017.
Pubchem CID 20335074, Retrieved from the Internet <URL:https://pubchem.ncbi.nlm.nih.gov/compound/20335074> ,2007 ,1-10.
Kean, et al., "Effect of R and S enantiomers of naproxen on aggregation and thromboxane production in human platelets", J Pharm Sci. 78(4), Apr. 1989, 324-327 (abstract only).
Mayer, "Stereo selective Metabolism of Anti-Inflammatory 2-arylpropionates", Acta Pharm Nord. 2 (3), 1990, 197-216 (abstract only).

* cited by examiner

2-BETA-NAPHTHYL-ACETIC ACID ANALOGS AS AKR1C3 INHIBITORS AND METHODS OF USING SAME

CROSS-REFERENCE TO RELATED APPLICATIONS

This present application is a 35 U.S.C. § 371 national phase application from, and claims priority to, International Application No. PCT/US2016/058075, filed Oct. 21, 2016, and published under PCT Article 21(2) in English, which claims priority under 35 U.S.C. § 119(e) to U.S. Provisional Application No. 62/244,934, filed Oct. 22, 2015, all of which are incorporated herein by reference in their entireties.

STATEMENT REGARDING FEDERALLY SPONSORED RESEARCH OR DEVELOPMENT

This invention was made with government support under CA 163227, ES013508, CA89450 and GM15431 awarded by National Institutes of Health. The government has certain rights in the invention.

BACKGROUND OF THE INVENTION

Hormone-dependent prostate malignancies are leading causes of cancer incidence and death worldwide. For example, prostate cancer (PC) is the second most common cancer in American men and responsible for about 11% of all cancer related deaths.

Since the pioneering studies of Charles Huggins, hormonal ablative therapy of PC has become standard practice. PC is initially dependent on testicular androgens and thus responsive to androgen ablation with surgical or chemical castration. The drug of choice for chemical castration is the luteinizing hormone-releasing hormone (LH-RH) agonist leuprolide. Leuprolide inhibits the release of LH from the anterior pituitary and prevents Leydig cell testosterone biosynthesis. Supplementation of castration with blockade of androgen action in the prostate is common and may be achieved with an androgen receptor (AR) antagonist (R-bicalutamide, also known as R-N-[4-cyano-3-(trifluoromethyl) phenyl]-3-[(4-fluorophenyl) sulfonyl]-2-hydroxy-2-methyl propanamide) or by inhibition of type 1 5α-reductase (SRD5A 1) and type 2 5α-reductase (SRD5A2) with dutasteride [(5α,17β)-N-{2,5 bis(trifluoromethyl) phenyl}-3-oxo-4-azaandrost-1-ene-17-carboxamide]. R-Bicalutamide is a relatively weak ligand for the AR, but in castration-resistant prostate cancer (CRPC) this compound can act as a weak agonist due to somatic mutations that may arise in AR. This highlights the need for improved agents to treat the disease.

In PC the therapeutic benefit of androgen deprivation therapy (ADT) is temporary and is often followed by recurrence of a more aggressive metastatic disease—CRPC. CRPC is characterized by elevated intratumoral androgen levels, increased AR signaling and expression of pro-survival genes despite castrate level circulating androgen concentrations. The development of CRPC in patients that have undergone ADT is driven by reactivation of AR signaling within the tumor. AR reactivation results from adaptive intratumoral androgen biosynthesis and from changes in the AR itself, including gene amplification, AR mutations that make the receptor ligand permissive, and the appearance of AR splice variants that make the receptor constitutively active.

The importance of the conversion of adrenal androgens into testosterone (T) and 5α-dihydrotestosterone (5α-DHT) or de novo androgen biosynthesis within the tumor is firmly established by the therapeutic efficacy of abiraterone acetate (Abi or AA); an inhibitor of P450c17 (17α-hydroxylase/17, 20 lyase) in CRPC patients. However, concerns over the need for co-administration of prednisone with Abi to prevent adrenal insufficiency and the rapid appearance of drug resistance indicates a pressing need for new therapeutic agents.

Aldo-keto reductase family 1, member C3 or aldo-keto reductase 1C3 (AKR1C3), also known as type 5, 17β-hydroxysteroid dehydrogenase (17β-HSD5), is a 17-ketoreductase that catalyzes the NADPH dependent conversion of androgen precursors, 4-androstene-3,17-dione ($\Delta^4$-AD) and 5α-androstan-3,17-dione (5-Adione) to yield the potent androgens, T and 5α-DHT, respectively. AKR1C3 also catalyzes the conversion of androsterone to 5α-androstane-3α,17β-diol, which is the precursor of 5α-DHT in the backdoor pathway. AKR1C3 is one of the most highly overexpressed steroidogenic enzymes in CRPC compared to normal prostate tissue and prostate cancer. Moreover, it is dramatically upregulated by ADT. Upon ADT, AKR1C3 is induced by the TMPRSS2-ERG fusion protein, whereby the ERG transcription factor can override the repressive effects of the AR binding to the AKR1C3 promoter. AKR1C3 also plays a role in resistance to P450c17 inhibition by Abi observed in prostate cancer cell lines and xenografts. AKR1C3 may also act as an AR selective coactivator that promotes tumor growth.

Enzalutamide (ENZ) is a AR super-antagonist used to treat CRPC patients, but this compound is plagued by drug resistance. AKR1C3 inhibitors can surmount ENZ resistance in prostate cell lines and xenografts, suggesting that AKR1C3 activity produces sufficient androgens to override the effects of this AR antagonist. Naproxen, (S)-2-(6-methoxy naphthalen-2-yl)propanoic acid, is a NSAID that is used clinically to block cyclooxygenase (COX) mediated inflammation. It is also a potent AKR1C3 inhibitor that inhibits the AKR1C3 catalyzed reduction of the bioreductive drug PR-104 in multiple human cancer cells lines and a lung cancer xenograft model. However, naproxen also inhibits AKR1C2, which limits its therapeutic potential in CRPC.

There is a need in the art for novel compounds that act as potent and selective inhibitors of AKR1C3. Such compounds could be used in the treatment of PC and/or CRPC. The present invention fulfills this need.

BRIEF SUMMARY OF THE INVENTION

The present invention relates to a novel class of AKR1C3 inhibitors and methods of using same.

The present invention provides at least one compound of the invention. The invention further provides a pharmaceutical composition comprising at least one compound of the invention and further comprising at least one pharmaceutically acceptable carrier. The invention further provides a method of treating, ameliorating or preventing cancer in a subject in need thereof. The invention further comprises a method of inhibiting aldo-keto reductase family 1, member C3 (AKR1C3) in a mammalian cell.

In certain embodiments, the compound of the invention is a compound of formula (I), or a salt, solvate or stereoisomer thereof, is

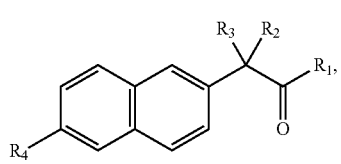

(I)

wherein: $R_1$ is selected from the group consisting of OH, —$NHSO_2(C_1-C_6$ alkyl), $C_1-C_6$ alkoxy and $C_3-C_8$ cycloalkoxy, wherein the alkyl, alkoxy or cycloalkoxy group is optionally substituted with at least one substituent selected from $C_1-C_6$ alkyl, $C_3-C_8$ cycloalkyl, optionally substituted aryl, OH, $C_1-C_6$ alkoxy, halo and —CN; $R_2$ and $R_3$ are independently selected from the group consisting of H, $C_1-C_6$ alkyl and $C_3-C_8$ cycloalkyl, wherein the alkyl or cycloalkyl is optionally substituted with at least one selected from the group consisting of $C_1-C_6$ alkyl and $C_3-C_8$ cycloalkyl; $R_4$ is selected from the group consisting of $C_1-C_6$ alkyl, $C_3-C_8$ cycloalkyl, $C_1-C_6$ alkoxy, $C_3-C_8$ cycloalkoxy, —$S(C_1-C_6$ alkyl), —$S(C_3-C_8$ cycloalkyl), —$S(=O)(C_1-C_6$ alkyl), —$S(=O)(C_3-C_8$ cycloalkyl), —$S(=O)_2(C_1-C_6$ alkyl) and —$S(=O)_2(C_3-C_8$ cycloalkyl); wherein the compound is not a compound wherein $R_1$ is OH, one of $R_2$ and $R_3$ is methyl and the other is H, and $R_4$ is methoxy.

In certain embodiments, $R_1$ is selected from the group consisting of OH and $C_1-C_6$ alkoxy, wherein the alkoxy group is optionally substituted with at least one substituent selected from $C_1-C_6$ alkyl, optionally substituted aryl, OH, $C_1-C_6$ alkoxy, halo and —CN. In other embodiments, $R_1$ is selected from the group consisting of OH and $C_1-C_6$ alkoxy. In yet other embodiments, $R_1$ is OH, methoxy, ethoxy, i-propoxy, n-propoxy, n-butoxy, i-butoxy, sec-butoxy or t-butoxy.

In certain embodiments, $R_2$ is H, and $R_3$ is selected from the group consisting of H, $C_1-C_6$ alkyl and $C_3-C_8$ cycloalkyl, wherein the alkyl or cycloalkyl is optionally substituted with at least one selected from the group consisting of $C_1-C_6$ alkyl and $C_3-C_8$ cycloalkyl.

In certain embodiments, $R_3$ is H, and $R_2$ is selected from the group consisting of H, $C_1-C_6$ alkyl and $C_3-C_8$ cycloalkyl, wherein the alkyl or cycloalkyl is optionally substituted with at least one selected from the group consisting of $C_1-C_6$ alkyl and $C_3-C_8$ cycloalkyl.

In certain embodiments, $R_2$ is H. In other embodiments, $R_3$ is methyl, ethyl, n-propyl, i-propyl, n-butyl, i-butyl, sec-butyl or t-butyl. In yet other embodiments, $R_3$ is H. In yet other embodiments, $R_2$ is methyl, ethyl, n-propyl, i-propyl, n-butyl, i-butyl, sec-butyl or t-butyl.

In certain embodiments, $R_2$ is H, and $R_3$ is methyl, ethyl, n-propyl, i-propyl, n-butyl, i-butyl, sec-butyl or t-butyl. In other embodiments, $R_3$ is H and $R_2$ is methyl, ethyl, n-propyl, i-propyl, n-butyl, i-butyl, sec-butyl or t-butyl.

In certain embodiments, $R_4$ is selected from the group consisting of $C_1-C_6$ alkyl, $C_1-C_6$ alkoxy, —$S(C_1-C_6$ alkyl), —$S(=O)(C_1-C_6$ alkyl) and —$S(=O)_2(C_1-C_6$ alkyl). In other embodiments, $R_4$ is methyl, methoxy, ethyl, ethoxy, thiomethyl, thioethyl, —$S(=O)CH_3$, $S(=O)_2CH_3$, —$S(=O)CH_2CH_3$ or —$S(=O)_2CH_2CH_3$.

In certain embodiments, the compound is selected from the group consisting of: 2-(6-ethylnaphthalen-2-yl)propanoic acid

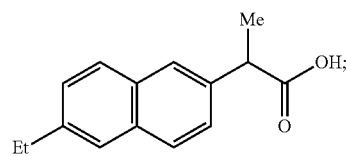

2-(6-ethoxynaphthalen-2-yl)propanoic acid

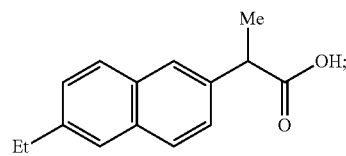

2-(6-(methylthio)naphthalen-2-yl)propanoic acid

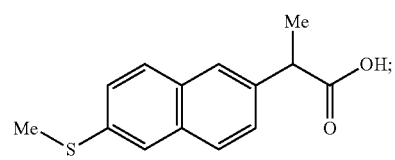 [SMILES: CSc1ccc2cc(C(C)C(=O)O)ccc2c1]

2-(6-(methylsulfinyl)naphthalen-2-yl)propanoic acid

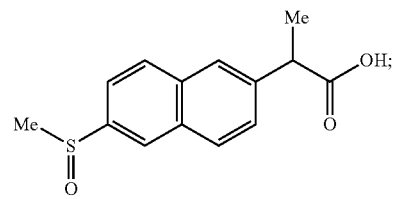 [SMILES: CC(C(=O)O)c1ccc2cc(S(C)=O)ccc2c1]

2-(6-(methylsulfonyl)naphthalen-2-yl)propanoic acid

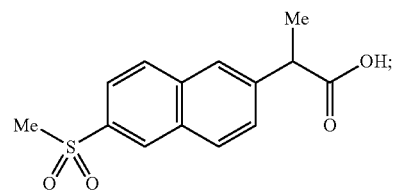 [SMILES: CC(C(=O)O)c1ccc2cc(S(C)(=O)=O)ccc2c1]

2-(6-methoxynaphthalen-2-yl)-N-(methylsulfonyl)butanamide

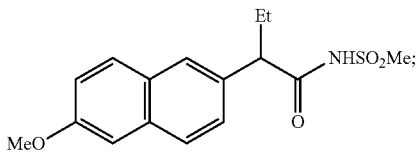

2-(6-methoxynaphthalen-2-yl)butanoic acid

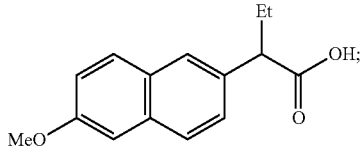 [SMILES: CCC(C(=O)O)c1ccc2cc(OC)ccc2c1]

2-(6-methoxynaphthalen-2-yl)-2-methylpropanoic acid

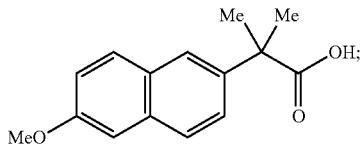 [SMILES: COc1ccc2cc(C(C)(C)C(=O)O)ccc2c1]

and 2-(6-methoxynaphthalen-2-yl)acetic acid

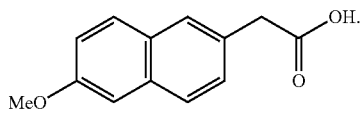 [SMILES: COc1ccc2cc(CC(=O)O)ccc2c1]

In certain embodiments, the compound is the compound of formula (Ia), or a salt or solvate thereof:

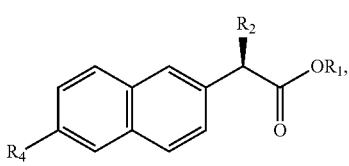

(Ia)

which has the (R) configuration at the carbon center linked to R₂.

In certain embodiments, the compound is the compound of formula (Ib), or a salt or solvate thereof:

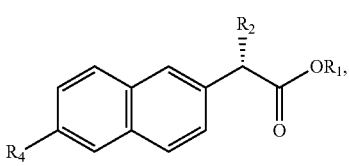

(Ib)

which has the (S) configuration at the carbon center linked to R₂.

In certain embodiments, the compound is selected from the group consisting of: 2(R)-(6-ethylnaphthalen-2-yl)propanoic acid; 2(R)-(6-ethoxynaphthalen-2-yl)propanoic acid; 2(R)-(6-(methylthio)naphthalen-2-yl)propanoic acid; 2(R)-(6-(methylsulfinyl)naphthalen-2-yl)propanoic acid; 2(R)-(6-(methylsulfonyl)naphthalen-2-yl)propanoic acid; 2(R)-(6-methoxynaphthalen-2-yl)-N-(methylsulfonyl)butanamide; and 2(R)-(6-methoxynaphthalen-2-yl)butanoic acid.

In certain embodiments, the compound is 2(R)-(6-methoxynaphthalen-2-yl) butanoic acid

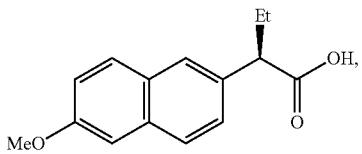

or a salt or solvate thereof.

In certain embodiments, the pharmaceutical composition further comprises at least one additional agent that treats or prevents cancer.

In certain embodiments, the method comprises administering to the subject a therapeutically effective amount of at least one compound of the invention.

In certain embodiments, the cancer comprises prostate cancer. In other embodiments, the cancer comprises castration-resistant prostate cancer. In yet other embodiments, the subject is human.

In certain embodiments, the method further comprises administering to the subject at least one therapeutic agent selected from the group consisting of indomethacin, desatinib, selegiline, seliciclib, TOK-001, SAHA, docetaxel, bevacizumab, taxotere, thalidomide, prednisone, Sipuleucel-T, cabazitaxel, enzalutamide, ARN-509, abiraterone, temozolomide, salts thereof, solvates thereof, and any mixtures thereof. In other embodiments, the compound and the at least one therapeutic agent are administered concomitantly to the subject. In yet other embodiments, the compound and the at least one therapeutic agent are coformulated.

In certain embodiments, the compound is a substrate-selective inhibitor of endocannabinoid oxygenation by cyclooxygenase-2 (COX-2). In other embodiments, the compound promotes analgesia in the subject suffering from prostate cancer and/or metastatic prostate cancer. In yet other embodiments, the compound is administered to the subject by a nasal, inhalational, topical, oral, buccal, rectal, pleural, peritoneal, intramuscular, subcutaneous, transdermal, epidural, intratracheal, otic, intraocular, intrathecal or intravenous route.

In certain embodiments, the method comprises contacting the cell with an effective amount of at least one compound of the invention. In other embodiments, the contacting does not significantly inhibit aldo-keto reductase family 1, member C1 (AKR1C1) and/or aldo-keto reductase family 1, member C2 (AKR1C2) in the cell.

In certain embodiments, the contacting inhibits less than about 5%, 10%, 20%, 30%, 40%, 50%, 60%, 70%, 80%, 90% or 95% of AKR1C1 and/or AKR1C2 in the cell.

In certain embodiments, the cell comprises a prostate cell. In other embodiments, the cell comprises a prostate cancer cell or a castration-resistant prostate cancer cell.

In certain embodiments, the cell is in vivo in the mammal.

In certain embodiments, the compound is administered to the subject by a nasal, inhalational, topical, oral, buccal, rectal, pleural, peritoneal, intramuscular, subcutaneous, transdermal, epidural, intratracheal, otic, intraocular, intrathecal or intravenous route.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 3A is a graph illustrating competitive inhibition of AKR1C3-catalyzed oxidation of S-tetralol by 8a. FIG. 3B is a graph illustrating competitive inhibition of AKR1C3-catalyzed reduction of $\Delta^4$-AD by 8a.

FIGS. 6A-6B comprise chromatographic traces relating to inhibition of testosterone formation in LNCaP-AKR1C3 cells with compound 8a. FIG. 6A shows conversion of 100 nM $\Delta^4$-AD to testosterone in LNCaP-AKR1C3 cells following digestion with β-glucurondiase. FIG. 6B shows the same experiment performed in the presence of 30 μM compound 8a.

FIG. 10A: oxidation reaction; FIG. 10B: reduction reaction. S=substrate, P=product and E=enzyme.

FIGS. 11A-11F comprise HPLC chromatograms of: FIG. 11A, (R)- and (S)-naproxen; FIG. 11B, (R)-naproxen; FIG. 11C, (S)-naproxen; FIG. 11D, compound 8 (racemic mixture); FIG. 11E, compound 8a; FIG. 11F, compound 8b.

DETAILED DESCRIPTION OF THE INVENTION

Figure 1:
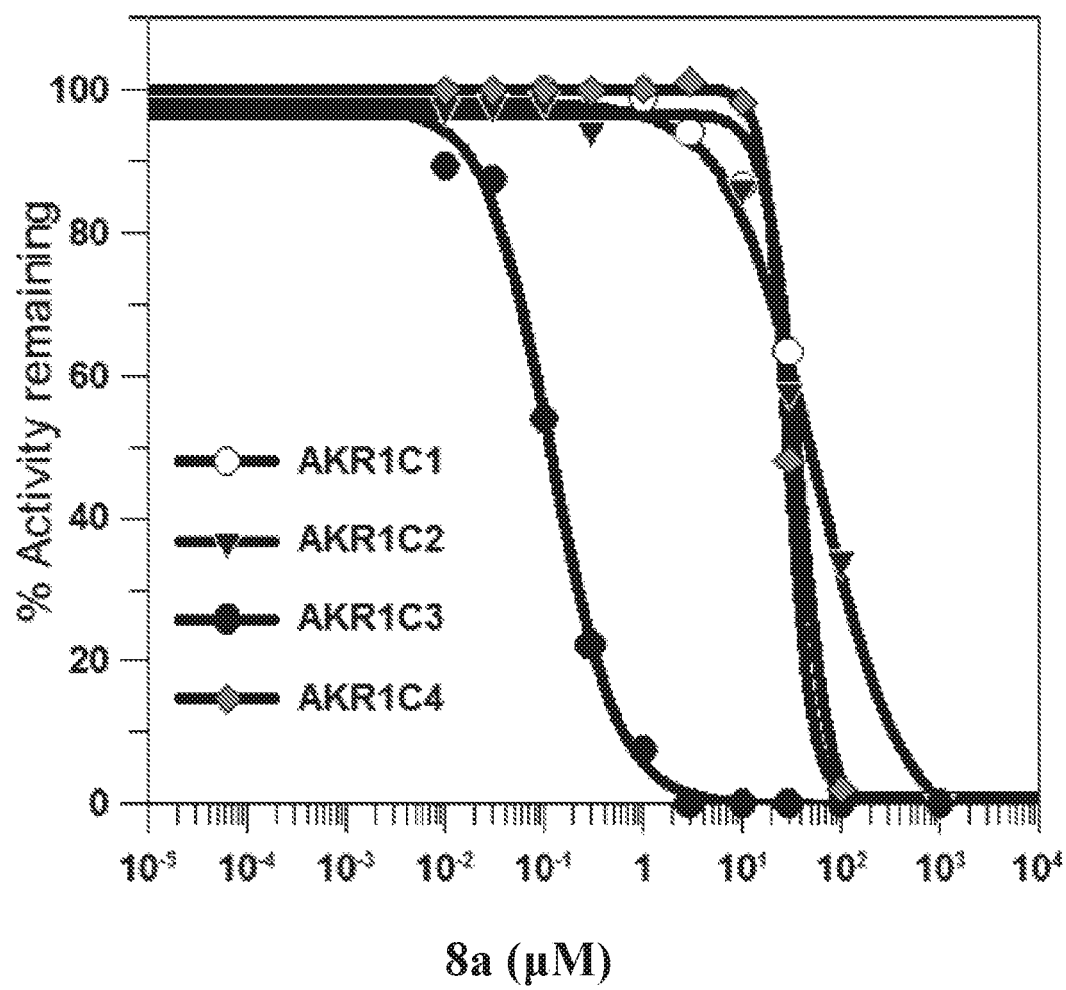
FIG. 1 is a graph illustrating the inhibitory effect of compound 8a on AKR1C1-4.

There is a need in the art for novel treatments for androgen-dependent cancers, such as prostate cancer (PC), including but not limited to castration-resistant prostate cancer (CRPC). AKR1C3 is overexpressed in PC, and is further up-regulated in CRPC. Multiple mechanisms contribute to the emergence of CRPC, but clinical trials with abiraterone acetate (Abi or AA) suggest that de novo synthesis of potent androgens within the prostate contribute to this disease stage. Indeed, the CRPC phenotype is characterized by elevated transcript levels for AKR1C3 and decreased transcript levels for 5α-reductase type 2, which results in an increased testosterone:5α-DHT ratio and indicates that testosterone (and not 5α-DHT) is the driver of CRPC.

AKR1C3 is thus an attractive target for treating of androgen-dependent cancers, since inhibitors of this enzyme would block the penultimate step in androgen biosynthesis within the prostate. However, a clinically useful inhibitor of AKR1C3 should not inhibit the closely related isoforms AKR1C1 and AKR1C2, as they are involved in steroid hormone inactivation in target tissues.

This invention includes the unexpected discovery of novel inhibitors of AKR1C3. The inhibitors of the invention exhibit selectivity for AKR1C3 over the enzymes AKR1C1 and AKR1C2, as well as COX-1 and COX-2 (otherwise known as Prostaglandin G/H synthases or PGHS).

In one aspect, the inhibitors of the invention find use in the treatment of androgen-driven proliferative disorders or diseases, such as but not limited to benign prostatic hyperplasia and prostate cancer, including but not limited to castration-resistant prostate cancer.

As demonstrated herein, the present studies identified (R)-2-(6-methoxy naphthalen-2-yl)butanoic acid as a potent AKR1C3 inhibitor. This compound competitively inhibited AKR1C3 and displayed selectivity for AKR1C3 over other AKR1C enzymes and COX. This compound was also efficacious at blocking AKR1C3 in a LNCaP-AKR1C3 cells (a model for CRPC cells). This compound is a therapeutic agent that can be used in the management of CRPC, either alone in combination with Abi or ENZ, where it may improve efficacy and reduce the incidence of resistance to other agents.

CRPC is currently treated with either Abi or ENZ, but patients rapidly develop drug resistance leading to an increase in median survival time of only 3-4 months. One mechanism of drug resistance is overexpression of AKR1C3. AKR1C3 is a "gatekeeper" for the production of potent androgens regardless of the pathway used and its ability to function as a coactivator for the AR. NSAIDs are known to be pan inhibitors of the AKR1C enzymes. The inhibition of AKR1C3 by NSAIDs is attained at therapeutic concentrations required for COX inhibition. As demonstrated herein, the present studies comprise structure activity relationship studies on the NSAID naproxen and have identified a R-enantiomer that differs from R-naproxen by the simple substitution of an ethyl group for a methyl group with therapeutic potential for CRPC.

In certain embodiments, the presence of small lipophilic groups at the 6-position or the β-carbon of naproxen is optimal for COX inhibitory activity. To determine the contribution of the 6-methoxy group to the inhibitory potency of naproxen for AKR1C3, analogs with small substituents were synthesized and evaluated. With the exception of the 6-thiomethoxy, all the other substituents at the 6-position did not significantly improve AKR1C3 potency or selectivity.

All the compounds evaluated were superior inhibitors of AKR1C3 than AKR1C2. Without wishing to be limited by any theory, because the AKR1C enzymes differ primarily in the enzyme subpockets, the larger and more flexible subpockets of AKR1C3 may allow for better interaction with the enzyme.

Figure 4:
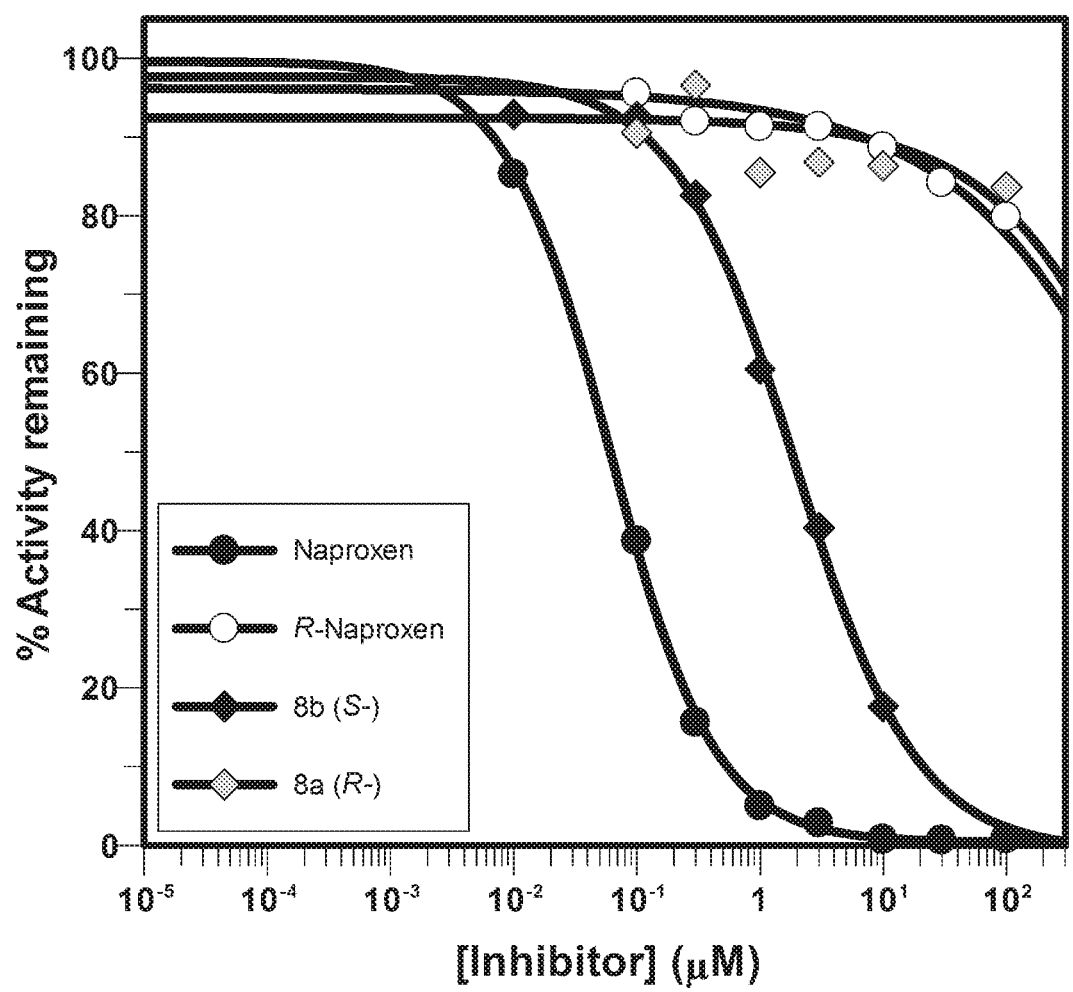
FIG. 4 is a graph illustrating inhibition of COX-1 by naproxen analogs.

Naproxen, with a chiral center at the α-carbon is used as the S-enantiomer for anti-inflammatory activity. This is due to the R-enantiomer being significantly less active as a COX inhibitor (FIG. 4). Naproxen is likewise a potent AKR1C3 inhibitor. Relative to naproxen, compound 1a was more potent as an AKR1C3 inhibitor and less potent as an AKR1C2 inhibitor, which translated into an increased selectivity for AKR1C3 relative to AKR1C2. To further explore this result, compound 8 with an α-ethyl group and its respective enantiomers 8a(R—) and 8b(S—) were subsequently evaluated. Similar stereochemical specificity was not apparent in the interaction of the enantiomers 8a and 8b with AKR1C3, but was observed with AKR1C2 as the two enantiomers displayed markedly different inhibitory potency towards AKR1C2. The different inhibitory potency of the enantiomers on AKR1C2 was subsequently confirmed using a steroidal substrate for AKR1C2. Modeling studies of enantiomers 8a and 8b indicate that they adopt remarkably distinct binding poses with AKR1C2 (FIG. 8).

Figure 8:
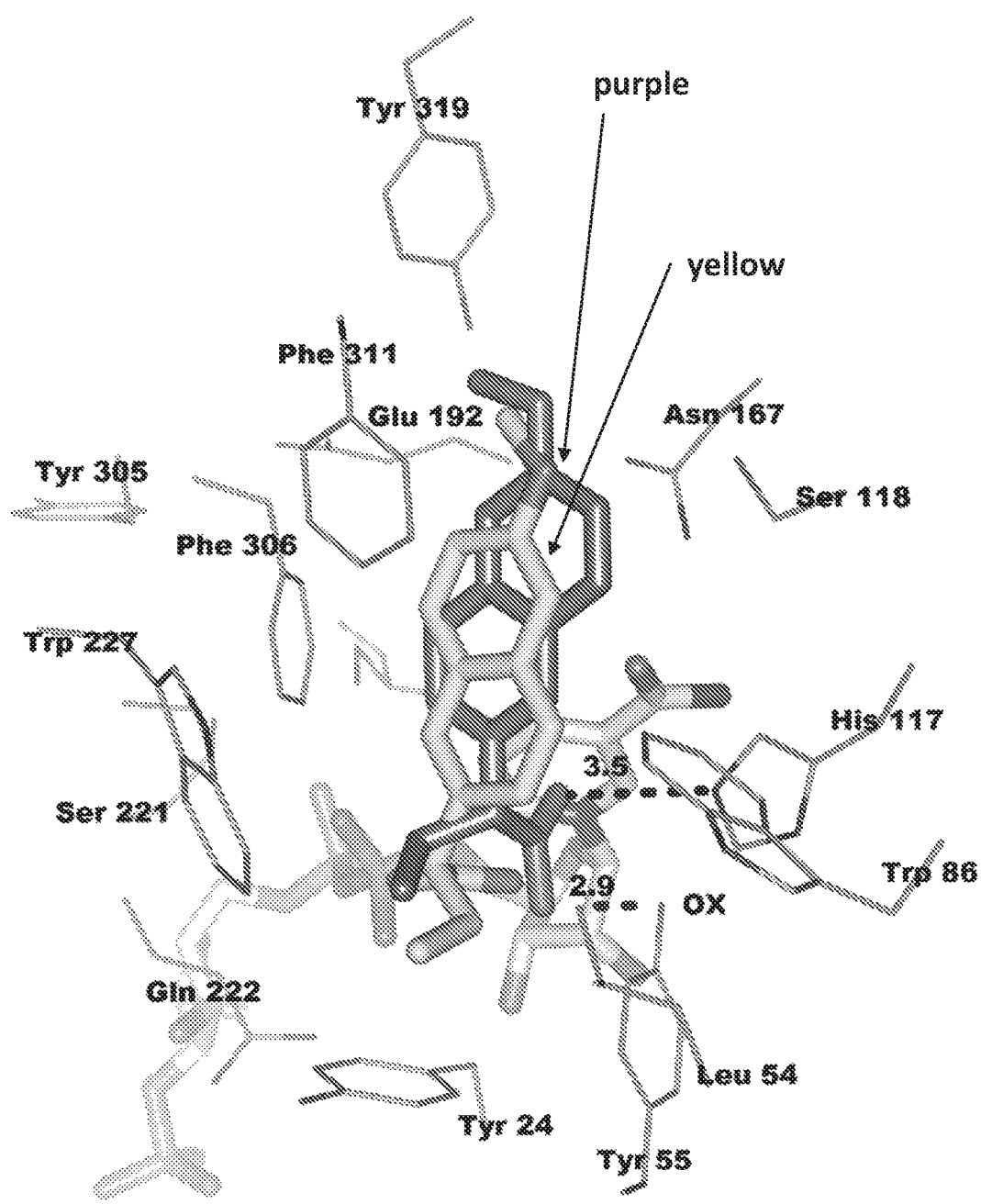
FIG. 8 is an illustration of the alignment of 8b and 8a in the AKR1C3 active site. AKR1C3 residues (green), 8b (yellow—lighter shade), 8a (purple—darker shade), dotted line: possible hydrogen bond; OX: oxyanion site (residues highlighted in pink), ligand alignments were performed using LigAlign plugin in Pymol. The template crystal structures of the AKR1C3·NADP$^+$ complexes were chosen from the RCSB protein data bank (PDB code: 3UFY and 3R58).

Ligand alignments of enantiomers 8a and 8b to the existing crystal structures (3UFY and 3R58) indicate that they adopt similar binding poses with AKR1C3 (FIG. 8). Both analogs 8a and 8b show a similar binding mode to that of R-naproxen with the ethyl group occupying the sub pocket 3 (SP3) formed by residues Tyr-24, Glu-192, Ser-217, Ser-221, and Gln-222. The remainder of the molecule extends into the Sub pocket 1 (SP1) pocket composed of Ser-18, Asn-167, Phe-306, Phe-311, and Tyr-319. The ligand alignments revealed closer proximity of carboxylic group of 8a compared to 8b at the oxyanion site (Tyr-55, His-117, and the NADP+ cofactor). A slight increase in inhibition activity and selectivity of 8a may be due to the favorable H-bond interaction with the oxyanion site.

Figure 9:
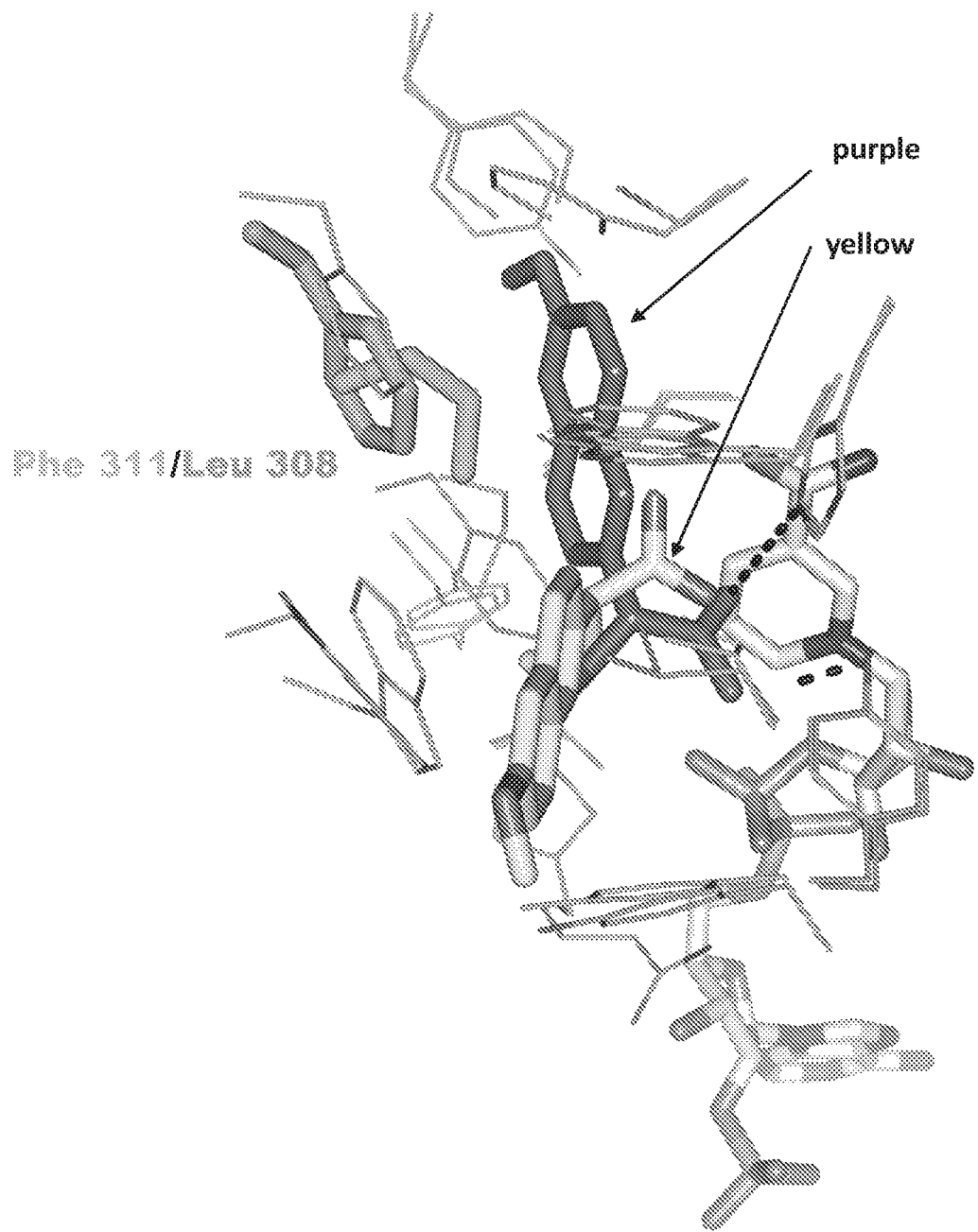
FIG. 9 is an illustration of 8b (yellow—lighter shade) and 8a (purple—darker shade) binding to AKR1C2 (green) and AKR1C3.

Compounds 8a and 8b display distinct binding poses with AKR1C2 (FIG. 9). While analog 8a binds in the active site of AKR1C2 similar to AKR1C3, compound 8b further extends into the SP3 pocket with no interaction with the SP1 pocket. An overlay structure of AKR1C2 onto AKR1C3 in the active site binding to 8a and 8b revealed additional selectivity of compound 8a. The Leu 308 side chain at the AKR1C2 binding site interacts sterically with 8a, which may significantly decrease its preference towards binding with the SP1 pocket of AKR1C2, resulting in a less inhibitory effect on AKR1C2.

Figure 10A:
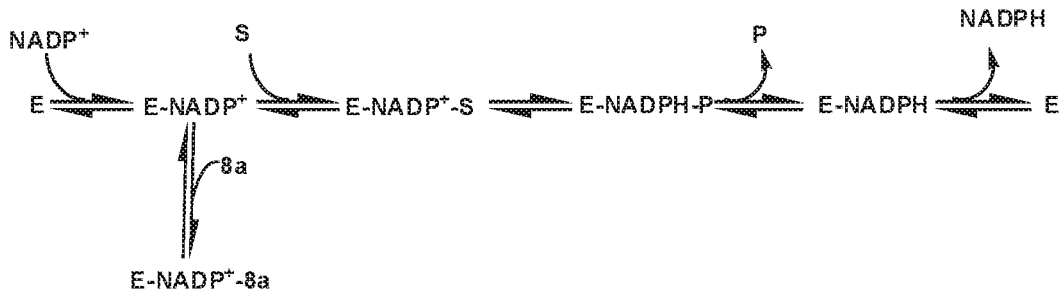
FIGS. 10A-10B illustrate mechanism of the reactions catalyzed by AKR1C3.
Figure 10B:
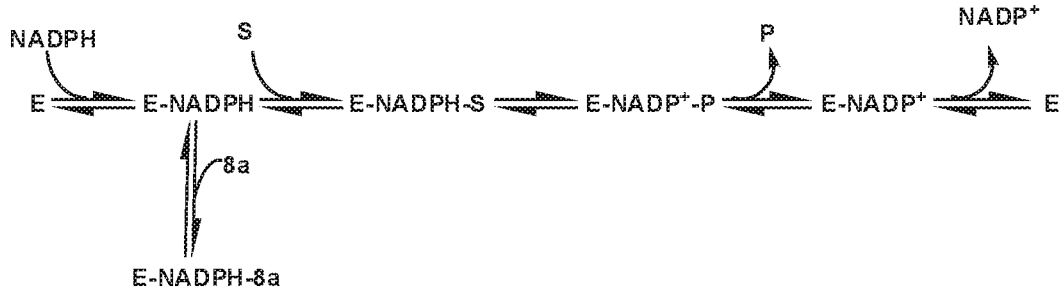
Figure 11A:
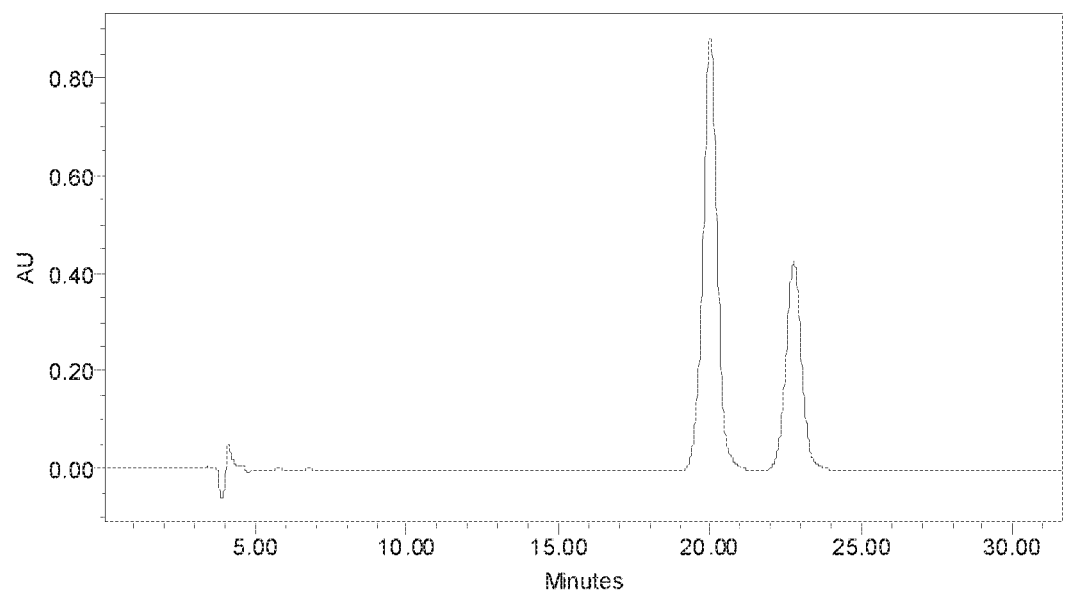
Figure 11B:
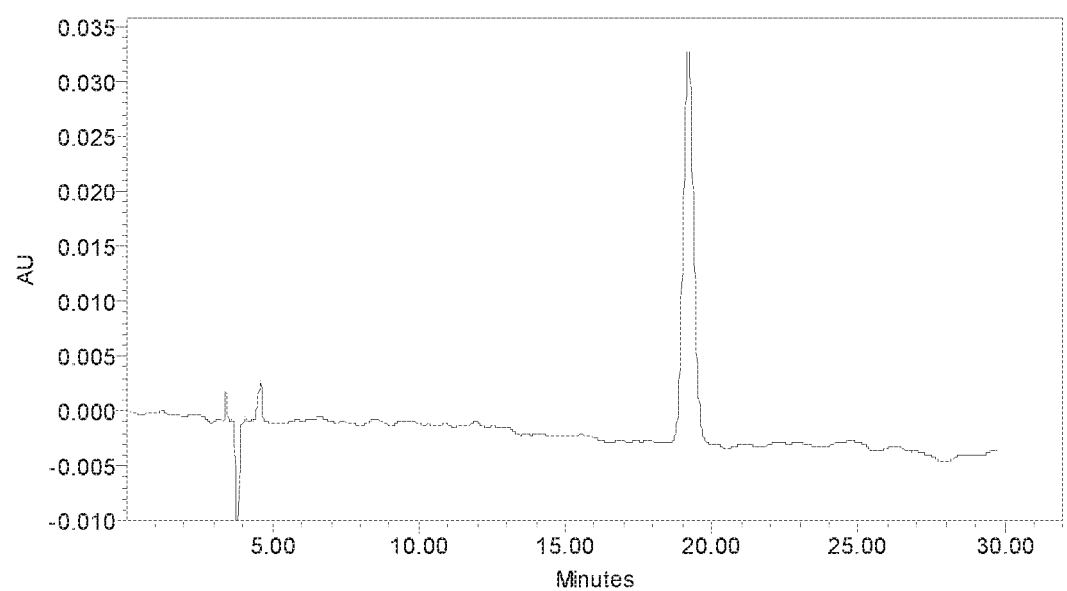
Figure 11C:
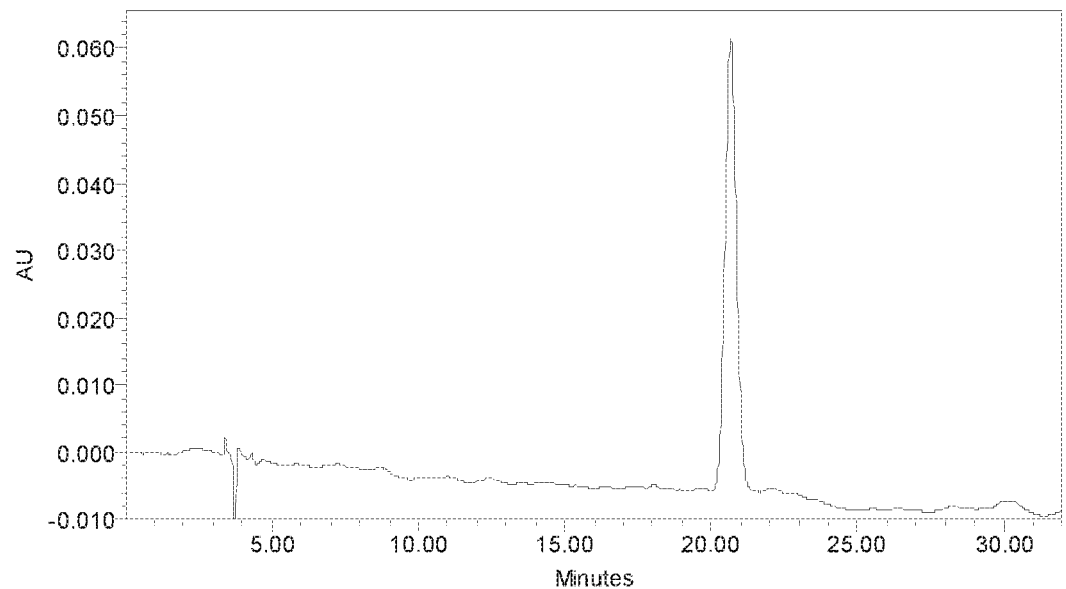
Figure 11D:
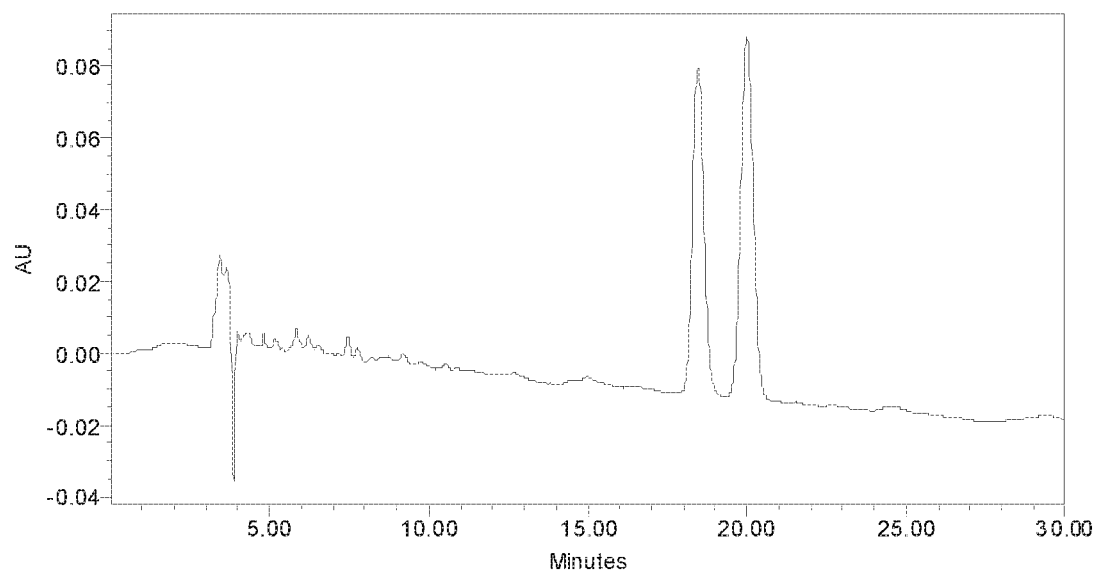
Figure 11E:
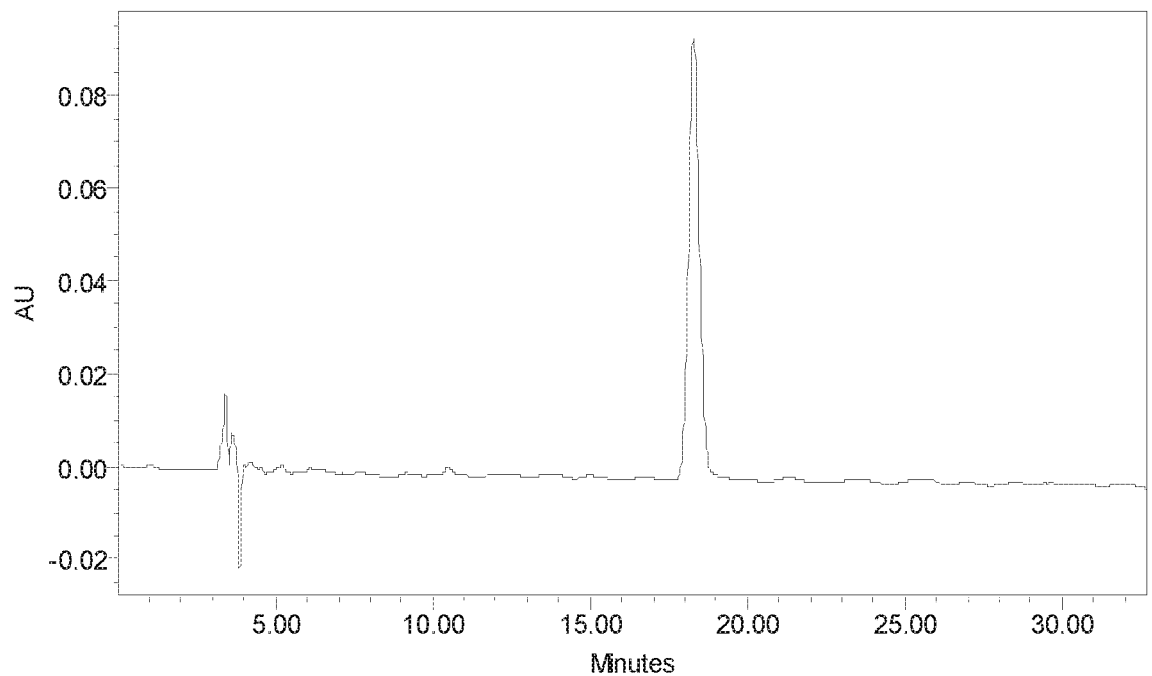
Figure 11F:
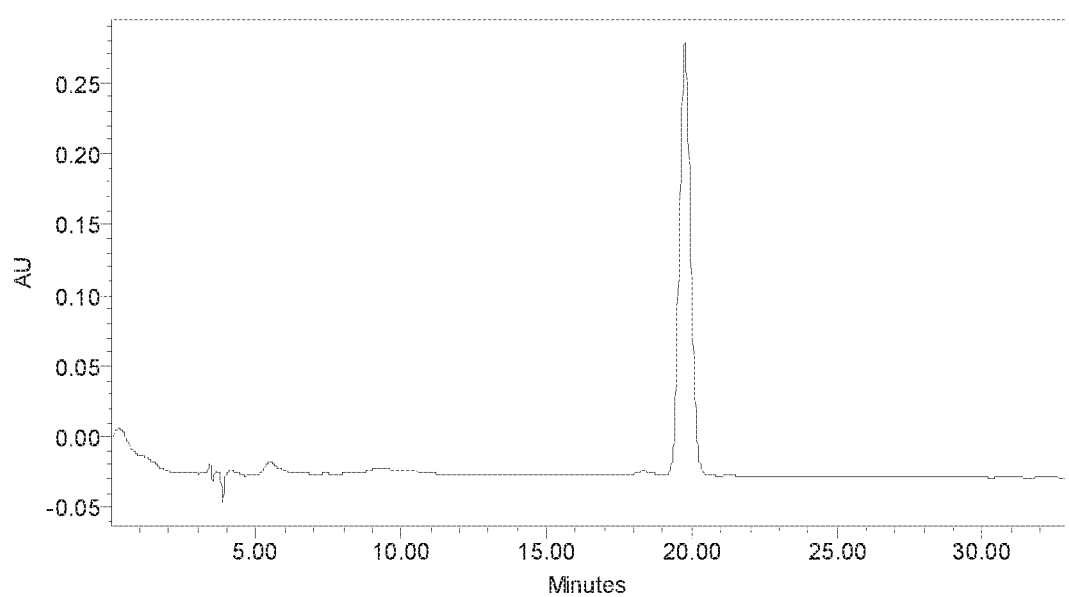

Compound 8a competes with S-tetralol and the physiologically relevant steroidal substrate, $\Delta^4$-AD for binding to AKR1C3, albeit with different binding constants. The difference in binding constant is related to the formation of two different inhibitor complexes. During the competitive inhibition of S-tetralol oxidation the E.NADP$^+$.I complex forms (where I=inhibitor) to yield a $K_i$=31 nM for 8a. By contrast during the competitive inhibition of $\Delta^4$-AD reduction the E.NADPH.I complex forms to yield a $K_i$=750 nM for 8a. Thus compound 8a displays a 20-fold preference for the E.NADP$^+$ complex (FIG. 10).

In certain embodiments, compound 8a with a negatively charged carboxylic acid group at pH 7 may interact with the positive charge of NADP$^+$, thus forming a stronger interaction with NADP$^+$ relative to NADPH. This could account for the lower $K_i$ value obtained for 8a in the oxidation of S-tetralol by AKR1C3 when compared to the value obtained in the reduction of $\Delta^4$-AD by AKR1C3.

Compound 8a had no effect on the transactivation of the AR mediated by 5α-DHT in HeLa cells, which express AKR1C3 endogenously. Thus, if AKR1C3 acts as an AR coactivator in these cells, then compound 8a differs from GTX560 in that it does not block co-activator function. Without wishing to be limited by any theory, this would suggest that not all competitive inhibitors of AKR1C3 are able to inhibit the co-activator function of this protein. However, co-activator function and its inhibition can be cell context dependent.

Consistent with the stereoselective inhibition of COX observed with naproxen, compound 8a was likewise devoid of inhibitory activity on COX. In certain embodiments, chronic COX inhibition is not desirable in the context of CRPC management.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in biochemistry, analytical chemistry and organic chemistry are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

As used herein, the term "AA" or "Abi" refers to abiraterone acetate, or a solvate or any other salt of the active compound.

The term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "A4-AD" refers to 4-androstene-3,17-dione, or a salt or solvate thereof.

As used herein, the term "ADT" refers to androgen deprivation therapy.

As used herein, the term "5α-DHT" refers to 5α-dihydrotestosterone.

As used herein, the term "AKR1C3" refers to aldo-keto reductase 1C3.

An "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half-life without adversely affecting activity of the peptide. Additionally, a disulfide linkage may be present or absent in the peptides.

As used herein, the term "AR" refers to the androgen receptor.

As used herein, the term "container" includes any receptacle for holding the pharmaceutical composition. For example, In certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject.

As used herein, the term "COX" refers to cyclooxygenases ($PGH_2$-synthase I and II).

As used herein, the term "CRPC" refers to castration-resistant prostate cancer.

The term "DNA" as used herein is defined as deoxyribonucleic acid. The term "RNA" as used herein is defined as ribonucleic acid. The term "recombinant DNA" as used herein is defined as DNA produced by joining pieces of DNA from different sources.

"Effective amount" or "therapeutically effective amount" are used interchangeably herein, and refer to an amount of a compound, formulation, material, or composition, as described herein effective to achieve a particular biological result. Such results may include, but are not limited to, the treatment of a disease or condition as determined by any means suitable in the art.

As used herein, the term "ENZ" refers to enzalutamide, or a salt or solvate thereof.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides: at least about 100 to about 500 nucleotides, at least about 500 to about 1000 nucleotides, at least about 1000 nucleotides to about 1500 nucleotides: or about 1500 nucleotides to about 2500 nucleotides; or about 2500 nucleotides (and any integer value in between).

As used herein, the term "fragment," as applied to a protein or peptide, refers to a subsequence of a larger protein or peptide. A "fragment" of a protein or peptide may be at least about 20 amino acids in length: for example at least about 50 amino acids in length: at least about 100 amino acids in length, at least about 200 amino acids in length, at least about 300 amino acids in length, and at least about 400 amino acids in length (and any integer value in between).

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. In certain embodiments, the subject is a human.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists or inverse agonists.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

An "isolated nucleic acid" refers to a nucleic acid segment or fragment that has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenine, "C" refers to cytosine, "G" refers to guanine, "T" refers to thymidine, and "U" refers to uracil.

As used herein, the term "NSAID" refers to nonsteroidal anti-inflammatory drug.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

As used herein, the term "PC" refers to prostate cancer.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth: malt; gelatin: talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol: esters, such as ethyl oleate and ethyl laurate: agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

As used herein, the terms "protein", "peptide" and "polypeptide" are used interchangeably, and refer to a compound comprised of amino acid residues covalently linked by peptide bonds. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Proteins" include, for example, biologically active fragments, substantially homologous proteins, oligopeptides, homodimers, heterodimers, protein variants, modified proteins, derivatives, analogs, and fusion proteins, among others. The proteins include natural proteins, recombinant proteins, synthetic proteins, or a combination thereof. A protein may be a receptor or a non-receptor.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the term "PSA" refers to prostate specific antigen.

As used herein, the term "receptor modulator" refers to a molecule or peptide that binds to at least one receptor in the body, affecting its activity, function or biological response. In some embodiments, a receptor modulator may act as an agonist, antagonist or inverse agonist. In some embodiments, the activity of a receptor modulator is dependent on the tissue localization of the receptor.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, arylaliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the terms SP1, SP2 and SP3 refers to subpockets 1, 2 and 3, respectively.

By the term "specifically binds," as used herein, is meant a molecule, such as an antibody or a small molecule, which recognizes and binds to another molecule or feature, but does not substantially recognize or bind other molecules or features in a sample.

As used herein, the term "TLC" refers to thin layer chromatography.

The term "treat" or "treating", as used herein, means reducing the frequency with which symptoms are experienced by a subject or administering an agent or compound to reduce the frequency and/or severity with which symptoms are experienced. As used herein, "alleviate" is used interchangeably with the term "treat." Treating a disease, disorder or condition may or may not include complete eradication or elimination of the symptom. The term "therapeutic" as used herein means a treatment and/or prophylaxis. A therapeutic effect is obtained by suppression, remission, or eradication of the diseases disclosed herein.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Exemplary are ($C_1$-$C_3$) alkoxy, such as, but not limited to, ethoxy and methoxy.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Exemplary is ($C_1$-$C_6$)alkyl, such as, but not limited to, ethyl, methyl, isopropyl, isobutyl, n-pentyl, n-hexyl and cyclopropylmethyl.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl. In certain embodiments, the substituted alkyl is not substituted with a hydroxy group.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Exemplary are phenyl and naphthyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl (benzyl). Exemplary is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Exemplary is substituted aryl ($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Exemplary is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Exemplary d is substituted heteroaryl-($CH_2$)—.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_8$)cycloalkyl, such as, but not limited to, cyclopropyl, cyclobutyl, cyclopentyl and cyclohexyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH═CH—O—CH$_3$, —CH═CH—CH$_2$—OH, —CH$_2$—CH═N—OCH$_3$, —CH═CH—N(CH$_3$)—CH$_3$, and —CH$_2$—CH═CH—CH$_2$—SH.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(═O)—CH$_3$. Up to two heteroatoms may be consecutive, such as, for example, —CH$_2$—NH—OCH$_3$, or —CH$_2$—CH$_2$—S—S—CH$_3$.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of C$_{1-6}$ alkyl, —OH, C$_{1-6}$ alkoxy, halo, amino, acetamido and nitro. As used herein, where a substituent is an alkyl or alkoxy group, the carbon chain may be branched, straight or cyclic, with straight being preferred.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds

Compounds useful within the methods of the invention may be synthesized using methodology described herein or any other techniques known in the art of organic synthesis, or may be obtained from commercial sources.

In one aspect, the compounds of the invention include a compound of formula (I), or a salt, solvate or stereoisomer thereof:

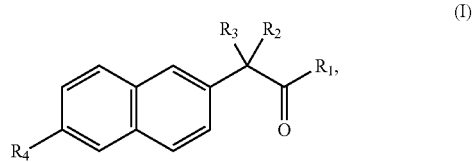

(I)

wherein:
R$_1$ is selected from the group consisting of OH, —NHSO$_2$(C$_1$-C$_6$ alkyl), C$_1$-C$_6$ alkoxy and C$_3$-C$_8$ cycloalkoxy, wherein the alkyl, alkoxy or cycloalkoxy group is optionally substituted with at least one substituent selected from C$_1$-C$_6$ alkyl, C$_3$-C$_8$ cycloalkyl, optionally substituted aryl (such as, but not limited to, optionally substituted phenyl), OH, C$_1$-C$_6$ alkoxy, halo and —CN;

$R_2$ and $R_3$ are independently selected from the group consisting of H, $C_1$-$C_6$ alkyl and $C_3$-$C_8$ cycloalkyl, wherein the alkyl or cycloalkyl is optionally substituted with at least one selected from the group consisting of $C_1$-$C_6$ alkyl and $C_3$-$C_8$ cycloalkyl;

$R_4$ is selected from the group consisting of $C_1$-$C_6$ alkyl, $C_3$-$C_8$ cycloalkyl, $C_1$-$C_6$ alkoxy, $C_3$-$C_8$ cycloalkoxy, —S($C_1$-$C_6$ alkyl), —S($C_3$-$C_8$ cycloalkyl), —S(=O)($C_1$-$C_6$ alkyl), —S(=O)($C_3$-$C_8$ cycloalkyl), —S(=O)$_2$($C_1$-$C_6$ alkyl) and —S(=O)$_2$($C_3$-$C_8$ cycloalkyl);

wherein the compound is not a compound wherein $R_1$ is OH, one of $R_2$ and $R_3$ is methyl and the other is H, and $R_4$ is methoxy.

In certain embodiments, $R_1$ is selected from the group consisting of OH and $C_1$-$C_6$ alkoxy, wherein the alkoxy group is optionally substituted with at least one substituent selected from $C_1$-$C_6$ alkyl, optionally substituted aryl (such as, but not limited to, optionally substituted phenyl), OH, $C_1$-$C_6$ alkoxy, halo and —CN. In other embodiments, $R_1$ is selected from the group consisting of OH and $C_1$-$C_6$ alkoxy. In yet other embodiments, $R_1$ is OH, methoxy, ethoxy, i-propoxy, n-propoxy, n-butoxy, i-butoxy, sec-butoxy or t-butoxy.

In certain embodiments, $R_2$ is H, and $R_3$ is selected from the group consisting of H, $C_1$-$C_6$ alkyl and $C_3$-$C_8$ cycloalkyl, wherein the alkyl or cycloalkyl is optionally substituted with at least one selected from the group consisting of $C_1$-$C_6$ alkyl and $C_3$-$C_8$ cycloalkyl. In certain embodiments, $R_3$ is H, and $R_2$ is selected from the group consisting of H, $C_1$-$C_6$ alkyl and $C_3$-$C_8$ cycloalkyl, wherein the alkyl or cycloalkyl is optionally substituted with at least one selected from the group consisting of $C_1$-$C_6$ alkyl and $C_3$-$C_8$ cycloalkyl. In yet other embodiments, $R_2$ is H, and $R_3$ is methyl, ethyl, n-propyl, i-propyl, n-butyl, i-butyl, sec-butyl or t-butyl. In yet other embodiments, $R_3$ is H and $R_2$ is methyl, ethyl, n-propyl, i-propyl, n-butyl, i-butyl, sec-butyl or t-butyl.

In certain embodiments, $R_4$ is selected from the group consisting of $C_1$-$C_6$ alkyl, $C_1$-$C_6$ alkoxy, —S($C_1$-$C_6$ alkyl), —S(=O)($C_1$-$C_6$ alkyl) and —S(=O)$_2$($C_1$-$C_6$ alkyl). In yet other embodiments, $R_4$ is methyl, methoxy, ethyl, ethoxy, thiomethyl, thioethyl, —S(=O)CH$_3$, S(=O)$_2$CH$_3$, —S(=O)CH$_2$CH$_3$ or —S(=O)$_2$CH$_2$CH$_3$.

In certain embodiments, the compound is selected from the group consisting of: 2-(6-ethylnaphthalen-2-yl)propanoic acid

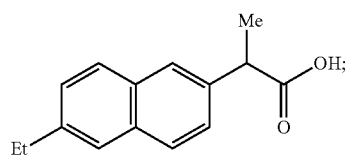 [SMILES: CCc1ccc2cc(C(C)C(=O)O)ccc2c1]

2-(6-ethoxynaphthalen-2-yl)propanoic acid

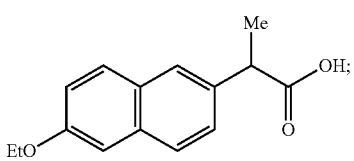 [SMILES: CCOc1ccc2cc(C(C)C(=O)O)ccc2c1]

2-(6-(methylthio)naphthalen-2-yl)propanoic acid

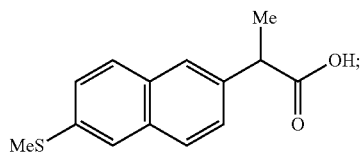 [SMILES: CSc1ccc2cc(C(C)C(=O)O)ccc2c1]

2-(6-(methylsulfinyl)naphthalen-2-yl)propanoic acid

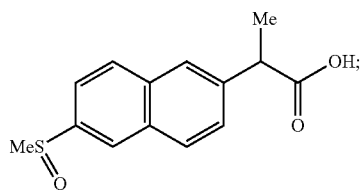

2-(6-(methylsulfonyl)naphthalene-2-yl)propanoic acid

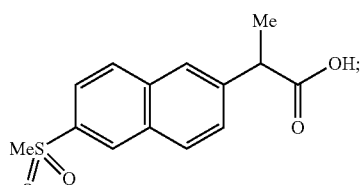

2-(6-methoxynaphthalen-2-yl)-N-(methylsulfonyl)butanamide

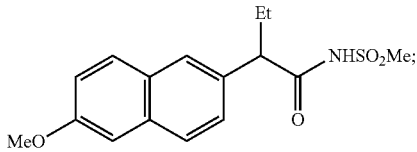

2-(6-methoxynaphthalen-2-yl)butanoic acid

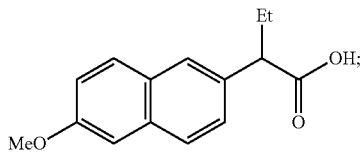

2-(6-methoxynaphthalen-2-yl)-2-methylpropanoic acid

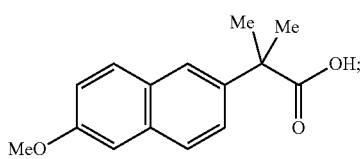 [SMILES: COc1ccc2cc(C(C)(C)C(=O)O)ccc2c1]

and 2-(6-methoxynaphthalen-2-yl)acetic acid

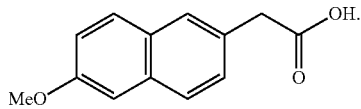 [SMILES: COc1ccc2cc(CC(=O)O)ccc2c1]

In certain embodiments, the compound is the compound of formula (Ia), or a salt or solvate thereof:

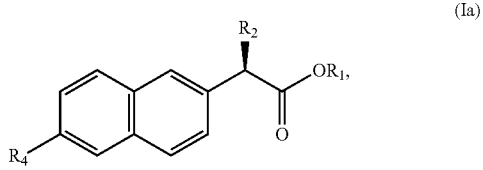

which has the (R) configuration at the carbon center linked to $R_2$.

In certain embodiments, the compound is the compound of formula (Ib), or a salt or solvate thereof:

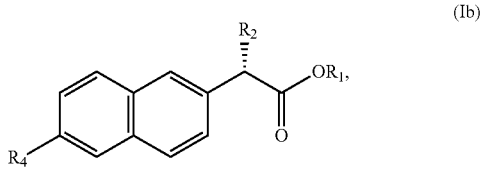

which has the (S) configuration at the carbon center linked to $R_2$.

In certain embodiments, the compound of formula (I) is selected from the group consisting of: 2(R)-(6-ethylnaphthalen-2-yl)propanoic acid; 2(R)-(6-ethoxynaphthalen-2-yl)propanoic acid; 2(R)-(6-(methylthio)naphthalen-2-yl)propanoic acid; 2(R)-(6-(methylsulfinyl)naphthalen-2-yl)propanoic acid; 2(R)-(6-(methylsulfonyl)naphthalen-2-yl)propanoic acid; 2(R)-(6-methoxynaphthalen-2-yl)-N-(methylsulfonyl)butanamide; and 2(R)-(6-methoxynaphthalen-2-yl)butanoic acid.

In certain embodiments, the compound is 2(R)-(6-methoxynaphthalen-2-yl)butanoic acid

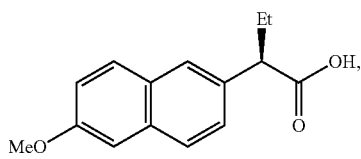

or a salt or solvate thereof.

The invention further provides pharmaceutical compositions comprising at least one compound of the invention and further comprising a pharmaceutically acceptable carrier.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention exist as tautomers. All tautomers are included within the scope of the compounds recited herein.

In certain embodiments, compounds described herein are prepared as prodrugs. A "prodrug" is an agent converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

Salts

The compounds described herein may form salts with acids or bases, and such salts are included in the present invention. In certain embodiments, the salts are pharmaceutically acceptable salts. The term "salts" embraces addition salts of free acids or free bases that are compounds of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base.

Methods

The invention includes a method of treating, ameliorating or preventing cancer in a subject in need thereof. The method comprises administering to the subject a therapeutically effective amount of at least one compound of the invention.

In certain embodiments, the cancer is PC. In other embodiments, the cancer is CRPC. In yet another embodiments, the subject is human.

In certain embodiments, the method further comprises administering to the subject at least one therapeutic agent selected from the group consisting of indomethacin, desatinib, selegiline, seliciclib, TOK-001, SAHA, docetaxel, bevacizumab, taxotere, thalidomide, prednisone, Sipuleucel-T, cabazitaxel, enzalutamide, ARN-509, abiraterone, temozolomide, mixtures thereof and salts thereof.

In certain embodiments, the compound and the at least one therapeutic agent are administered concomitantly to the subject. In another embodiment, the compound and the at least one therapeutic agent are coformulated.

In certain embodiments, the compound is a substrate-selective inhibitor of endocannabinoid oxygenation by COX-2. In other embodiments, the compound promotes analgesia (i.e., alleviates and/or treats pain) in the subject suffering from metastatic prostate cancer.

The invention further includes a method of inhibiting AKR1C3 in a cell. The method comprises contacting the cell with an effective amount of at least one compound of the invention. In certain embodiments, the contacting does not inhibit AKR1C1 and/or AKR1C2 in the cell. In certain embodiments, the contacting inhibits less than about 5%, 10%, 20%, 30%, 400%, 50%, 60/%, 70%, 80%, 90% or 95% of AKR1C1 and/or AKR1C2 in the cell. In other embodiments, the cell comprises a prostate cell. In yet embodiments, the cell comprises a PC cell and/or a PRPC cell. In yet embodiments, the cell is in vivo in a mammal. In yet other embodiments, the mammal is human.

In certain embodiments, the compound is administered to the subject by a nasal, inhalational, topical, oral, buccal, rectal, pleural, peritoneal, intramuscular, subcutaneous, transdermal, epidural, intratracheal, otic, intraocular, intrathecal or intravenous route.

Combination Therapies

In one aspect, the compounds contemplated within the invention are useful in the methods of present invention in combination with one or more agents useful in the treatment of cancer, such as prostate cancer. These additional agents may comprise compounds of the present invention or agents (such as commercially available compounds) known to treat, prevent, or reduce cancer, such as prostate cancer. In certain embodiments, the combination of a compound contemplated within the invention and a chemotherapeutic agent has additive, complementary or synergistic effects in the treatment of cancer, such as prostate cancer, in a subject, or prevention of cancer, such as prostate cancer, in a subject. In another embodiment, the combination of a compound contemplated within the invention and an agent used to treat cancer, such as prostate cancer, has additive, complementary or synergistic effects in the treatment of cancer, such as prostate cancer, in a subject, or prevention of cancer, such as prostate cancer, in a subject.

In certain embodiments, the therapeutic agents that may be used to treat prostate cancer include:
indomethacin (2-{1-[(4-chlorophenyl)carbonyl]-5-methoxy-2-methyl-1H-indol-3-yl}acetic acid),
desatinib (N-(2-chloro-6-methylphenyl)-2-[[6-[4-(2-hydroxyethyl)-1-piperazinyl]-2-methyl-4-pyrimidinyl]amino]-5-thiazole carboxamide monohydrate),
selegiline ((R)—N-methyl-N-(1-phenylpropan-2-yl)prop-2-yn-1-amine),
seliciclib (2-(R)-(1-Ethyl-2-hydroxyethylamino)-6-benzylamino-9-isopropylpurine),
TOK-001 (VN/124-1; (3β)-17-(1H-benzimidazol-1-yl)androsta-5,16-dien-3-ol),
SAHA ($N^1$-hydroxy-$N^8$-phenyl-octanediamide),
docetaxel (1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}),
bevacizumab (Avastin), taxotere (1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}), thalidomide ((RS)-2-(2,6-dioxopiperidin-3-yl)-1H-isoindole-1,3(2H)-dione), prednisone ((8S,9S,10R,13S,14S,17R)-17-hydroxy-17-(2-hydroxy acetyl)-10,13-dimethyl-7,8,9,10,12,13,14,15,16,17-decahydro-3H-cyclopenta[α]phenanthrene-3,11(6H)-dione), Provenge (Sipuleucel-T or APC8015), cabazitaxel ((1S,2S,3R,4S,7R,9S,10S,12R,15S)-4-(Acetyloxy)-15-{[(2R,3S)-3-{[(tert- butoxy)carbonyl]amino}-2-hydroxy-3-phenylpropanoyl]oxy}-1-hydroxy-9,12-dimethoxy-10,14,17,17-tetramethyl-11-oxo-6-oxatetracyclo[11.3.1.0$^{3,10}$.0$^{4,7}$]heptadec-13-ene-2-yl), enzalutamide (4-(3-(4-cyano-3-(trifluoromethyl)phenyl)-5,5-dimethyl-4-oxo-2-thioxoimidazolidin-1-yl)-2-fluoro-N-methylbenzamide), ARN-509 (4-(7-(6-cyano-5-(trifluoromethyl)pyridin-3-yl)-8-oxo-6-thioxo-5,7-diazaspiro[3.4]octan-5-yl)-2-fluoro-N-methylbenzamide), abiraterone ((3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-ol), and temozolomide (TMZ; 4-methyl-5-oxo-2,3,4,6,8-pentazabicyclo-[4.3.0]-nona-2,7,9-triene-9-carboxamide).

In certain embodiments, the compounds useful within the invention and the therapeutic agents are administered concomitantly to said subject. The term "concomitantly" indicates that the compounds useful within the invention and the agents are administered to the subject at the same time or within a limited interval of time (such as 4 hours, 2 hours, 1 hour, 30 minutes, 15 minutes, 5 minutes or 1 minute, or any fraction thereof) of each other. In another embodiment, the compounds useful within the invention and the therapeutic agents are co-formulated.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Pharmaceutical Compositions and Therapies

Administration of a compound useful within the invention may be achieved in a number of different ways, using methods known in the art. The therapeutic and prophylactic methods of the invention thus encompass the use of pharmaceutical compositions comprising the compounds useful within the invention to practice the methods of the invention. The pharmaceutical compositions useful for practicing the invention may be administered to deliver a dose of 1 ng/kg/day to 100 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Although the description of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Typically, dosages that may be administered in a method of the invention to an animal, preferably a human, range in amount from 0.5 μg to about 50 mg per kilogram of body weight of the animal. While the precise dosage administered will vary depending upon any number of factors, including but not limited to, the type of animal and type of disease state being treated, the age of the animal and the route of administration, the dosage of the compound will preferably vary from about 1 μg to about 10 mg per kilogram of body weight of the animal. More preferably, the dosage will vary from about 3 μg to about 1 mg per kilogram of body weight of the animal.

Pharmaceutical compositions that are useful in the methods of the invention may be prepared, packaged, or sold in formulations suitable for oral, parenteral, topical, buccal, or another route of administration. Other contemplated formulations include projected nanoparticles, liposomal preparations, resealed erythrocytes containing the active ingredient, and immunologically-based formulations.

The formulations of the pharmaceutical compositions described herein may be prepared by any method known or hereafter developed in the art of pharmacology. In general, such preparatory methods include the step of bringing the active ingredient into association with a pharmaceutically acceptable carrier or one or more other accessory ingredients, and then, if necessary or desirable, shaping or packaging the product into a desired single- or multi-dose unit.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents: inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A specific preservative is a combination of about 0.5% to 2.0% benzyl alcohol and 0.05% to 0.5% sorbic acid.

The composition may include an anti-oxidant and a chelating agent that inhibits the degradation of the compound. Exemplary antioxidants for some compounds are BHT, BHA, alpha-tocopherol and ascorbic acid in the exemplary range of about 0.01% to 0.3% and more preferably BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropyl methylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative.

Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Controlled- or sustained-release formulations of a composition of the invention may be made using conventional technology, in addition to the disclosure set forth elsewhere herein. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the compositions of the invention.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, nanoparticles, or microspheres or a combination thereof that facilitates the controlled-release of the active ingredient.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed: the time of administration: the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated, each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In certain embodiments, the compositions of the invention are administered to the subject in dosages that range from one to five times per day or more. In other embodiments, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 0.1 mg to about 1,000 mg, about 0.2 mg to about 950 mg, about 0.4 mg to about 900 mg, about 1 mg to about 850 mg, about 5 mg to about 750 mg, about 20 mg to about 700 mg, about 30 mg to about 600 mg, about 50 mg to about 500 mg, about 75 mg to about 400 mg, about 100 mg to about 300 mg, about 120 mg to about 250 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1.000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a composition of the invention, alone or in combination with a second pharmaceutical agent; and instructions for using the composition to treat, prevent, or reduce one or more symptoms of a disease in a subject.

Administration

Routes of administration of any of the compositions of the invention include oral, nasal, rectal, parenteral, sublingual, transdermal, transmucosal (e.g., sublingual, lingual, (trans) buccal, (trans)urethral, (intra)nasal, and (trans)rectal), intravesical, intrapulmonary, intraduodenal, intragastrical, intrathecal, subcutaneous, intramuscular, intradermal, intraarterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as a film coating system sold under the trademark OPADRY™ available from Colorcon, West Point, Pa. (e.g., the trademarks OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example.

Other acceptable diluents and solvents include, but are not limited to, Ringer's solution, isotonic sodium chloride solution, and fixed oils such as synthetic mono- or di-glycerides. Other parentally-administrable formulations that are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

A pharmaceutical composition of the invention may be prepared, packaged, or sold in a formulation suitable for topical administration. There are several advantages to delivering compounds, including drugs or other therapeutic agents, into the skin (dermal drug delivery) or into the body through the skin (transdermal drug delivery). Transdermal compound delivery offers an attractive alternative to injections and oral medications. Dermal compound delivery offers an efficient way to deliver a compound to the skin of a mammal, and preferably a human, and provides a method of treatment of the skin, or otherwise provides a method of affecting the skin, without the need to break or damage the outer layer of the skin.

In the present invention, dermal delivery, by way of a dermally-acting compound of the invention, provides these advantages for treatment of a skin-related condition, disorder or disease.

A number of compounds, including some drugs, will penetrate the skin effectively simply because the molecules are relatively small and potent at small doses of 0.1 mg to 15 mg/day (Kanikkannan et al., 2000, Curr. Med. Chem. 7:593-608). Many other compounds and drugs can be delivered only when an additional enhancement system is provided to "force" them to pass through the skin. Among several methods of transdermal drug delivery are electroporation, sonophoresis, iontophoresis, permeation enhancers (cyclodextrins), and liposomes. While the aforementioned methods are also included in the present invention for dermal delivery of the compounds of the invention, liposomes represent an exemplary dermal delivery method.

The composition of the invention may consist of the active ingredient alone, in a form suitable for administration to a subject, or the composition may comprise at least one active ingredient and one or more pharmaceutically acceptable carriers, one or more additional ingredients, or some combination of these. The active ingredient may be present in the composition in the form of a physiologically acceptable ester or salt, such as in combination with a physiologically acceptable cation or anion, as is well known in the art. Compositions of the invention will also be understood to encompass pharmaceutical compositions useful for treatment of other conditions, disorders and diseases associated with the skin.

In one aspect, a dermal delivery vehicle of the invention is a composition comprising at least one first compound that can facilitate dermal delivery of at least one second compound associated with, or in close physical proximity to, the composition comprising the first compound. As will be understood by the skilled artisan, when armed with the disclosure set forth herein, such delivery vehicles include, but should not be limited to, liposomes, nanosomes, phospholipid-based non-liposome compositions (eg., selected cochleates), among others.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 0.001% to about 90% (w/w) active ingredient, although the concentration of the active ingredient may be as high as the solubility limit of the active ingredient in the solvent. Formulations for topical administration may further comprise one or more of the additional ingredients described herein.

In one aspect of the invention, a dermal delivery system includes a liposome delivery system, and that the present invention should not be construed to be limited to any particular liposome delivery system. Based on the disclosure set forth herein, the skilled artisan will understand how to identify a liposome delivery system as being useful in the present invention.

The present invention also encompasses the improvement of dermal and transdermal drug delivery through the use of penetration enhancers (also called sorption promoters or accelerants), which penetrate into skin to reversibly decrease the barrier resistance. Many compounds are known in the art for penetration enhancing activity, including sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes. Other enhancers include oleic acid, oleyl alcohol, ethoxydiglycol, laurocapram, alkanecarboxylic acids, dimethylsulfoxide, polar lipids, or N-methyl-2-pyrrolidone.

In alternative embodiments, the topically active pharmaceutical or cosmetic composition may be optionally combined with other ingredients such as moisturizers, cosmetic adjuvants, anti-oxidants, chelating agents, surfactants, foaming agents, conditioners, humectants, wetting agents, emulsifying agents, fragrances, viscosifiers, buffering agents, preservatives, sunscreens and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art.

In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

Additional components may include, but should not be limited to those including water, oil (eg., olive oil/PEG7), biovera oil, wax (eg., jojoba wax), squalene, myristate (eg., isopropyl myristate), triglycerides (eg., caprylic triglyceride), Solulan 98, cocoa butter, shea butter, alcohol (eg., behenyl alcohol), stearate (eg., glycerol-monostearate), chelating agents (eg., EDTA), propylene glycol, SEPIGEL (Seppic, Inc., Fairfield, N.J.), silicone and silicone derivatives (eg., dimethicone, cyclomethicone), vitamins (eg., vitamin E), among others.

Buccal Administration

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein.

Alternately, formulations suitable for buccal administration may comprise a powder or an aerosolized or atomized solution or suspension comprising the active ingredient.

Such powdered, aerosolized, or aerosolized formulations, when dispersed, preferably have an average particle or droplet size in the range from about 0.1 to about 200 nanometers, and may further comprise one or more of the additional ingredients described herein.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475; 6,488,962; 6,451,808; 5,972,389; 5,582,837 and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology, using for example proteins equipped with pH sensitive domains or protease-cleavable fragments. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In certain embodiments, the compounds of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Kits

The invention also includes a kit comprising a compound useful within the methods of the invention and an instructional material that describes, for instance, administering the compound to a subject as a prophylactic or therapeutic treatment for cancer, for example prostate cancer, as described elsewhere herein. In an embodiment, the kit further comprises a (preferably sterile) pharmaceutically acceptable carrier suitable for dissolving or suspending the therapeutic composition, comprising the compound useful within the methods of the invention, for instance, prior to administering the molecule to a subject. Optionally, the kit comprises an applicator for administering the compound.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in the experiments and the results of the experiments presented in these Examples are now described.

Methods
Synthesis:

All commercially available reagents and anhydrous solvents were ACS grade or better and were used as received.

Analytical thin-layer chromatography was carried out using glassbacked plates coated with fluorescent silica gel 60 F254 from Whatman (Partisil LK6D). Spots were visualized under natural light and UV illumination at $\lambda$=254 and 365 nm. Flash chromatography was conducted on a Biotage SP1 automated flash chromatography system equipped with a fixed wavelength UV detector ($\lambda$=254 nm). Samples were preabsorbed onto ready-made silica gel samplets and then applied on to normal-phase flash chromatography cartridges (Biotage KP-SIL, size according to requirements) and elution with a 0-100% EtOAc/hexane (0.5% acetic acid) gradient. $^1$H and $^{13}$C NMR spectra were recorded at 400 and 100 MHz, respectively, using a Bruker AV-400 with sample changer (BACS 60). A purity of ≥95% (unless otherwise indicated) for the final compounds in this study was confirmed by analytical HPLC on a Waters HPLC system with PDA detector (set at $\lambda$=254 nm) equipped with a Supelco Supelcosil LC-18 reverse-phase column (15 cm Å~3 mm, 5 µm). Compounds screened in the current study also were characterized with respect to their melting point (mp) and HRMS.

Ligand Alignments:

Ligand alignments were performed using a LigAlign v1.0 plugin (University of Toronto) installed onto Pymol v1.7.6 (Schrödinger). The crystal structures of AKR1C3·NADP$^+$ complexed with R-naproxen (PDB code: 3UFY), AKR1C3·NADP$^+$ complexed with S-naproxen (PDB code: 3R58) and AKR1C2·NADP$^+$ complexed with S-naproxen (PDB codes: 4JQ1) were used as templates. The structure of AKR1C2·NADP$^+$ complexed with R-naproxen was obtained by docking R-naproxen on to existing AKR1C2 structure (PDB codes: 4JQ1). Water molecules and original ligands were removed from the structures and hydrogens were manually added using AutoDockTools-1.5.6 (Scripps Research Institute). Ligands (R-naproxen, 8b and 8a) were generated as PDB files using Chem 3D Pro 14.0 (Cambridgesoft). All ligand bonds were identified as flexible. Parameters for gridbox were determined from the original ligand binding sites (AKR1C3: center_x=7.283, center_y=−5.571, center_z=−10.669, size_x=40, size_y=40, size_z=40 AKR1C2: center_x=−75.397, center_y=142.774, center_z=247.606, size_x=40, size_y=40, size_z=40). Docking experiments were performed using AutoDock Vina (Scripps Research Institute).

Enzyme Purification: Homogenous recombinant enzymes AKR1C1-4 were prepared and purified (Burczynski, et al., 1998, Biochemistry 37:6781-6790). Enzymes were purified to constant specific activity and their purity established by SDS-PAGE. All AKR enzymes were stored at −80° C. in 20 mM potassium phosphate buffer pH 7.0 containing 30% glycerol, 1 mM EDTA, and 1 mM β-mercaptoethanol. Under standard assay conditions, the specific activity of AKR1C1 for the NAD$^+$ dependent oxidation of 1-acenaphthenol (Sigma) was 2.0 µmol min$^{-1}$ mg$^{-1}$. The specific activities of AKR1C2 and AKR1C3 for the NAD$^+$ dependent oxidation of S-tetralol (Sigma) were 1.5 and 2.0 µmol min$^{-1}$ mg$^{-1}$, respectively, and the specific activity of AKR1C4 for the NAD$^+$ dependent oxidation of androsterone (Steraloids) was 0.3 µmol min$^{-1}$ mg$^{-1}$. The specific activities of AKR1C enzymes were determined by measuring the formation of NADH at 340 nm using a Beckman DU640 spectrophotometer. A typical assay solution contained 100 mM potassium phosphate pH 7.0, 2.3 mM NAD$^+$, 200 µM 1-acenaphthenol for AKR1C1, 3.0 mM Stetralol for AKR1C2 and 1C3, and 75 µM androsterone for AKR1C4, 4% acetonitrile (v/v). The mixtures were incubated at 25° C. (AKR1C1 and 1C4) or 37° C. (AKR1C2 and 1C3) for 3 min, followed by adding a serial dilution of enzyme solution to a final volume of 1 mL to initiate the reaction. After continuously monitoring for 5 min, the increase in UV absorption using different concentrations of enzyme were recorded to calculate the initial velocity of substrate oxidation and determine enzyme-specific activity.

COX-1 was purified to homogeneity from ram seminal vesicles (Smith, et al., 2000, Arch Biochem Biophys 375: 195-200). The purity of the enzyme was assessed by SDS-PAGE. The specific activity of COX-1 for the conversion of arachidonic acid to prostaglandin $H_2$ ($PGH_2$) was coupled to the oxidation of N,N,N',N'-tetramethyl-1,4-phenylenediamine (TMPD) and was found to be 1.0 µmol min$^{-1}$ mg$^{-1}$. The specific activity of COX-1 enzyme was determined by measuring the formation of oxidized TMPD at 610 nm using Synergy 2 plate reader (BioTek). A typical assay solution (200 µL) contained 100 mM Tris-HCl (pH 8.0), 2 µM Hemin (Sigma), 5% DMSO, a serial dilution of COX-1 enzyme solution, 80 µM TMPD (Sigma), and 20 µM arachidonic acid (Sigma). Reagents were mixed and incubated at 25° C. for 5 min followed by adding a mixture of TMPD and arachidonic acid to initiate the reaction. Specific activity was determined based on the initial velocity of the reduction of $PGG_2$ formed in the reaction.

All AKR enzymes were stored at −80° C. in 20 mM potassium phosphate buffer pH 7.0 containing 30% glycerol, 1 mM EDTA and 1 mM β-mercaptoethanol. SDS-PAGE of the homogenous enzymes showed that each protein was more than 92% pure based on analysis using GelQuant NET V 1.8.2 provided by BiochemLabSolutions dot com.

Enzyme Assays:

S-Tetralol Oxidation Assay:

the inhibitory potency of the individual compounds against the AKR1C isoforms was determined by monitoring the NADP$^+$ dependent oxidation of S-tetralol catalyzed by the AKR1C enzymes using substrate concentrations at their $K_m$ values in the presence and absence of varying concentration of the inhibitors (Adeniji, et al., 2012, J Med Chem 55:2311-2323). Reaction systems (200 µL) contained 100 mM potassium phosphate buffer (pH 7.0), 4% DMSO, 200 µM NADP$^+$, a serial dilution of compounds, S-tetralol, and AKR1C enzymes. The concentration of S-tetralol used in the inhibition assays using AKR1C1, 1C2, 1C3, and 1C4 was 5, 22.5, 165, and 25 µM, respectively, which was equal to their $K_m$ values in order to make a direct comparison of $IC_{50}$ values. The concentration of AKR1C1, 1C2, 1C3, and 1C4 was 111, 86, 95, and 552 nM, respectively. Reagents were mixed and incubated at 37° C. for 10 min followed by adding AKR1C enzymes to initiate the reaction. A continuous fluorometric assay (Ex, 340 nm; Em, 460 mM) to measure NADPH formation was conducted at 37° C. for 5 min, and the $IC_{50}$ value of each compound was calculated. To determine the pattern of inhibition, five fixed concentrations of S-tetralol were used and four different concentrations of inhibitor were used and a gobal fit of the equations for COMP, NONCOMP and UNCOMP to the data was applied using Grafit.

Steroid Reduction:

Compounds were tested for their ability to inhibit the AKR1C3 catalyzed, reduction of [$^3$H]-$\Delta^4$-AD and the AKR1C2 catalyzed reduction of [$^3$H]-5α-DHT. Compounds were incubated with purified recombinant enzyme and radiolabeled steroid in 100 mM phosphate buffer pH7.0 and 4% DMSO at 37° C. The reaction was initiated by the addition of 1 mM NADPH, aliquots were removed over time and subsequently quenched by the addition of ice cold ethyl acetate. The ethyl acetate fraction was extracted and dried in vacuum. Steroid reference standards and extracts were dissolved in 50 µl ethyl acetate and applied to LK6D Silica TLC plates (Whatman Inc., Clifton, N.J.). TLC plates were developed using a dichloromethane/ethyl acetate (80:20 v/v) solution and were scanned with a Bioscan System 200 plate reader (Washington, D.C.). The percentage of radioactivity in the product peak was calculated assuming that the combined radioactivity in the substrate and product peaks was 100%. Initial velocities were computed by converting the percentage of radioactivity in the product peak by the specific radioactivity of the starting material to generate pmoles/min. The pattern of AKR1C3 inhibition was determined using five fixed concentrations of [$^3$H]-$\Delta^4$-AD using 5 concentrations of inhibitor. Equations for COMP, NON-COMP and UNCOMP were fitted to the data as described elsewhere herein.

Cox-1 Assay:

The effect of the compounds on COX-1 activity was determined by a continuous colorimetric assay that monitored the oxidation of N, N, N, N-tetramethyl-1,4-phenylenediamine (TMPD) when coupled to the COX catalyzed formation of $PGH_2$ from $PGG_2$ using arachidonic acid as substrate. In brief, 200 µL of reaction solution was composed of 100 mM Tris-HCl (pH 8.0), 2 µM Hemin (Sigma), 5% DMSO, a serial dilution of compounds, COX-1 enzyme (175 nM), 80 µM TMPD (Sigma), and 20 µM arachidonic acid (Sigma). Reagents were mixed and incubated at 25° C. for 5 min followed by adding a mixture of TMPD and arachidonic acid to initiate the reaction. A continuous colorimetric assay to measuring TMPD oxidation at 610 nm was conducted using a Synergy 2 plate reader at 25° C. for 5 min, and $IC_{50}$ value of each compound was calculated (Adeniji, et al., 2012, J Med Chem 55:2311-2323).

AR-Luciferase Assay:

HeLa13 (Cherian, et al., 2012, J. Biol. Chem. 287:23368-23380) cells stably expressing the AR and a luciferase reporter gene construct were used for this assay as previously described (Chen, et al., 2012, Bioorg. & Med. Chem Letts. 22:3492-3497). Briefly, cells were cultured in phenol red free media supplemented with 5% CDFBS (CSS media) for 48 h. The cells were then harvested and plated in a 96 well plate for 6-7 h after which fresh CSS media containing x nM 5α-DHT in the presence of inhibitor was added. After 20 h incubation, the media was removed and the luciferase activity in the cells was measured using the Bright Glo kit (Promega) according to the manufacturer's instructions. Fold induction of luciferase was evaluated relative to untreated cells.

Cell-Based Assays:

Western Blot:

LNCaP cells stably expressing AKR1C3 (LNCaP-AKR1C3 cells) (Byrns, et al., 2012, J. Steroid. Biochem. & Mol. Biol. 130:7-15) seeded at a density of 1.5×10$^6$ cells were plated in 6 cm dishes containing phenol red free RPMI-1640 media supplemented with 5% CDFBS, 1% Pen/Strep and 2 mM L-Glutamine (CSS media). The cells were incubated for 24 h after which media was aspirated and fresh CSS media containing 100 nM $\Delta^4$-AD plus and minus inhibitors. The cells were incubated for 24 h after which they were harvested in RIPA lysis buffer supplemented with protease inhibitors at 4° C. Lysate protein concentration was determined by the Bradford assay using the BIORAD protein dye (Bio-Rad). The samples were subjected to electrophoresis on a 12% SDS-PAGE gel that was subsequently transferred to a nitrocellulose membrane. The membrane was probed with the appropriate antibodies as follows; anti β-tubulin (Millipore, #05-661) anti-PSA (Meridian Life Science, Inc., #K92110R). Blots were imaged using the ECL reagent (Pierce) and GelDoc XR+ System and Image Lab software (Bio-Rad).

Radiometric Assay of Androgen Metabolism:

LNCaP-AKR1C3 cells seeded at a density of 1.5×10$^6$ cells were plated in 6 well plates in CSS media. The cells were allowed to incubate for 24 h, after which the media was aspirated and fresh CSS media with 7.5 nM (1.26 μCi) of [$^3$H] $\Delta^4$-AD and 92.5 nM of cold $\Delta^4$-AD (to obtain a final concentration of 100 nM) was added in the presence and absence of 30 μM of compound 8a in each well. The cells were incubated for 48 h, after which time the media was collected for analysis (Byrns, et al., 2012, J. Steroid. Biochem. & Mol. Biol. 130:7-15). The media was extracted twice with cold ethyl acetate. In order to determine radioactivity of each phase, a portion of each fraction was added to Ultima Gold (Perkin Elmer Life Sciences) scintillation fluid and analyzed on a TriCarb 2100 (Packard Instruments, Perkin Elmer Life Sciences), all CPM counts were blank-adjusted and reported as corrected cpm. The aqueous phases were acidified to pH 6.5 with acetic acid and subjected to treatment with 400 U of *E. coli* β-glucuronidase at 37° C. for 24 h. The de-conjugated androgens were re-extracted as described elsewhere herein, dried in vacuum and re-dissolved in 100 μL ethyl acetate for separation on the multi-channel LK6D Silica TLC plates. Plates were developed using dichloromethane/ethyl acetate (80:20 v/v) and scanned on the BioScan 200 plate reader.

Determination of the Configuration of Naproxen Enantiomers:

The configuration of compounds was inferred by comparing the order of elution of the two enantiomers (4a and 4b; 8a and 8b) from a chiral column with the order of elution of naproxen and R-naproxen from the same column.

A mixture of R- and S-naproxen, R-naproxen, S-naproxen, compound 4, 4a, and 4b were resolved on a Chiral AD-RH column (150 mm×4.6 mm) using an isocratic elution method with a mobile phase of 60% HPLC grade water: 40% acetonitrile containing 0.1% formic acid.

Naproxen, R-naproxen, a mixture of naproxen and R-naproxen, compound 8, 8a and 8b were resolved on a Chiral-Pak IC column (150 mm×4.6 mm) using an isocratic elution method. The mobile phase was 0.05% TFA in Hexane: 0.05% TFA in EtOH (98.5%:1.5%) with a flow rate of 0.5-1.0 ml/min at room temperature. Absorbance was monitored at 230 nm except for compounds 4a and 4b where absorbance was monitored at 254 nm.

Example 1: AKR1C3 and AKR1C2 Inhibitor Screening

Naproxen analogs were synthesized to explore the effect of modifications of its structure on AKR1C3 activity and selectivity. Certain synthesized compounds were carboxylic acids. Modifications were made primarily on the α-carbon or the 6-position of the naphthalene ring. Due to the presence of the chiral center in the molecule, most of compounds (compounds 2-8) were initially assayed as racemates and screened for AKR1C2 and AKR1C3 inhibition without separation of the enantiomers.

S-Naproxen 1 was the precursor of certain compounds disclosed herein (Schemes 1-2). A common intermediate was S-methyl-2-(6-trifluoromethylsulfonyloxy naphthalene propanoate (D). This compound was synthesized from S-naproxen, which was converted to O-demethyl naproxen (B) under acidic conditions followed by esterification to yield C. Subsequent addition of trifluoromethane sulfonic anhydride in base gave D. Compound D was converted to compound E (compound 2) via the 6-vinylogous intermediate and deesterification. The protected acid C was converted to the ethoxy intermediate using iodoethane and desesterification and gave compound F (compound 3). Coupling of D with sodium triisopropylsilanethiolate followed by deprotection with tetrabutylammonium fluoride gave (S)-2-(6-(methylthio)naphthalen-2-yl)propanoate H, which upon base hydrolysis yielded the racemic acid I (compound 4). The racemic acid was further oxidized with m-chloroperoxybenzoic acid to yield racemic 2-(6-methylsulfinyl)naphthalene-2-yl)-propanoic acid J (compound 5). The steps to compound K (compound 6) are identical except the final oxidation of the methyl-thio derivative to yield the methylsufonyl derivative used potassium peroxymonosulfate (Oxone). Compound N (compound 8) was synthesized in two steps from 2-bromo-6-methoxy-naphthalene L. Compound O (compound 7) was synthesized from racemic N (compound 8) via 1,1'-carbonyldiimidazole coupling of methanesulfonamide.

Scheme 1. Synthesis of Racemic Naproxen Analogs.

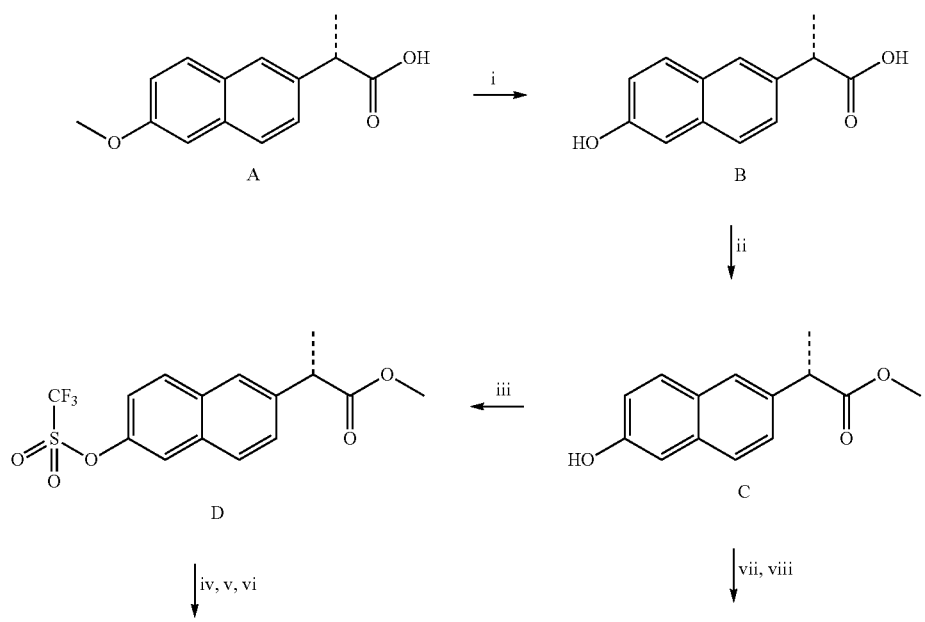

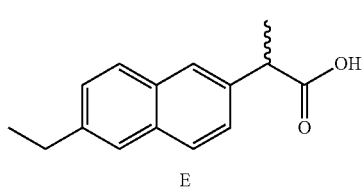
E
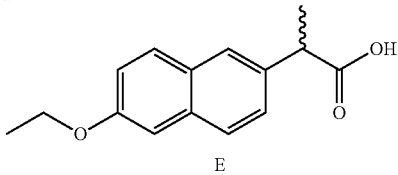
E
Reagents and conditions: (i) 48% HBr, AcOH, reflux, 3 h; (ii) TMSCl, CH$_3$OH, 25° C., 2 h; (iii) (CF$_3$SO$_2$)$_2$O, Et$_3$N, DCM, 25° C., 1 h; (iv) CH$_2$=CHBF3K, Cs$_2$CO$_3$, Pd(PPh$_3$)$_4$, Et$_3$N, EtOH, 50° C., 16 h; (v) (OAc)$_2$Pd, t-But$_3$P, HCO$_2$H, 25° C., 12 h; (vi) 3M KOH/CH$_3$OH, reflux, 3 h; (vii) KOH/C$_2$H$_5$I, 25° C., 30 min; (viii) 3M KOH/CH$_3$OH, reflux, 2 h.
Scheme 2. Synthesis of Racemic Naproxen Analogs.
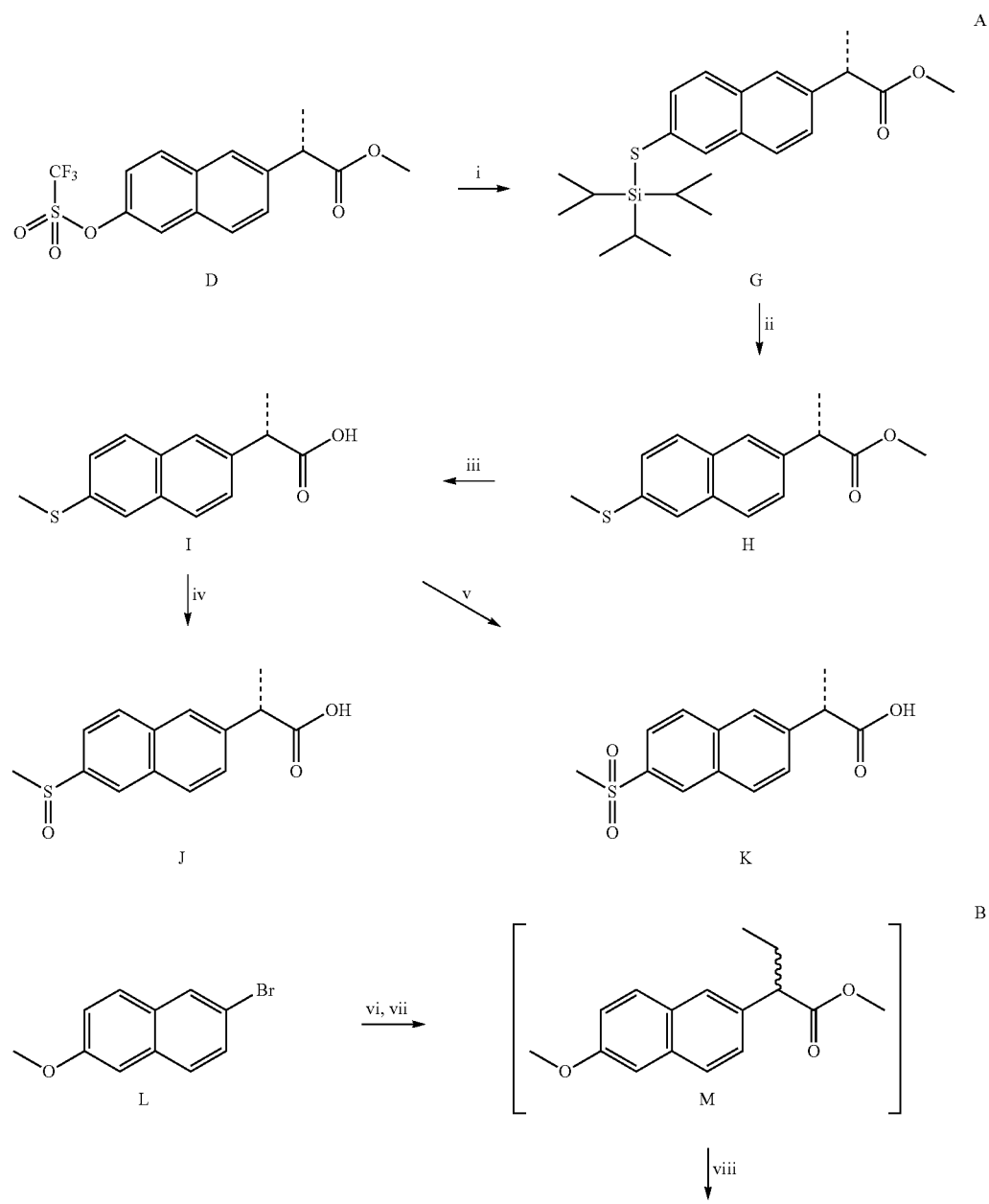

-continued

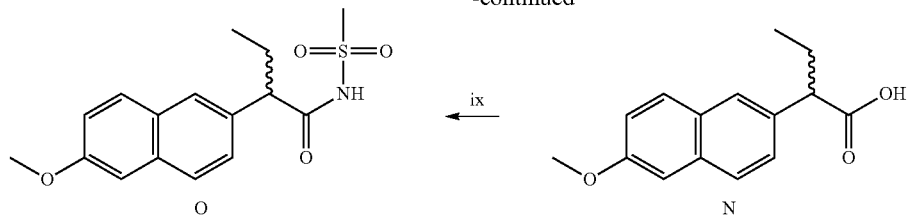

Reagents and conditions: (i) Pd(PPh$_3$)$_4$, [(CH$_3$)$_2$CH]$_3$SiSH, C$_6$H$_6$, reflux, 4 h; (ii) TBAF, CH$_3$I, 25° C., 2 h; (iii) 3M KOH/CH$_3$OH, reflux, 2 h; (iv) mCPBA, DCM 0° C., 1 h; (v) KHSO$_5$·0.5KHSO$_4$·0.5K$_2$SO$_4$, (CH$_3$)$_2$C=O/H$_2$O, 25° C., 2 h; (vi) Mg, I$_2$, THF, reflux, 1 h; (vii) CH$_3$CH$_2$CHBrCO$_2$CH$_3$, THF, reflux, 2 h; (viii) 3M KOH/CH$_3$OH, reflux, 2 h, (ix) CDI, CH$_3$SO$_2$NH$_2$, DBU, DCM, 25° C., 4 h.

The ability of the compounds to inhibit the NADP$^+$ dependent oxidation of S-tetralol catalyzed by AKR1C3 and AKR1C2 was determined and IC$_{50}$ values obtained (Table 1). Since the S-tetralol assays were performed at K$_m$ the IC$_{50}$ values for the two enzymes were directly comparable. Naproxen inhibited AKR1C3 with an IC$_{50}$, value of 180 nM and was not selective for AKR1C3 over AKR1C2.

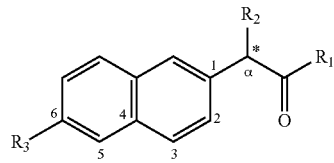

TABLE 1

Structure and AKR1C3/AKR1C2 Inhibitory Potency of Naproxen Analogs

| Compound | R$_1$ | R$_2$ | R$_3$ | AKR1C3 IC$_{50}$ (µM) | AKR1C2 IC$_{50}$ (µM) | Ratio IC$_{50}$ value (AKR1C2/AKR1C3) |
|---|---|---|---|---|---|---|
| S-Naproxen (1) | —OH | —Me | —OMe | 0.18 ± 0.04 | 1.26 ± 0.15 | 7 |
| R-Naproxen (1a) | —OH | —Me | —OMe | 0.05 ± 0.004 | 2.75 ± 0.35 | 56 |
| LM5751(±) 2 | —OH | —Me | —Et | 0.12 ± 0.0075 | 1.9 ± 0.11 | 15 |
| LM5753(±) 3 | —OH | —Me | —OEt | 0.10 ± 0.0076 | 2.4 ± 0.24 | 24 |
| LM5752(±) 4 | —OH | —Me | —SMe | 0.060 ± 0.0054 | 1.5 ± 0.14 | 25 |
| (R)-4a | —OH | —Me | —SMe | 0.05 ± 0.0015 | 4.35 ± 0.61 | 87 |
| (S)-4b | —OH | —Me | —SMe | 0.07 ± 0.004 | 1.35 ± 0.09 | 19 |
| LM5754(±) 5 | —OH | —Me | —S(=O)Me | 1.05 ± 0.13 | 6.3 ± 0.35 | 6 |
| LM5754(±) 6 | —OH | —Me | —S(=O)$_2$Me | 0.82 ± 0.1 | 3.0 ± 0.14 | 4 |
| LM5885 (±) 7 | —NHSO$_2$Me | —Et | —OMe | 6.0 ± 1.0 | 34 ± 1.8 | 6 |
| LM5750(±) 8 | —OH | —Et | —OMe | 0.12 ± 0.014 | 7.6 ± 0.95 | 58 |
| LM5750B 8a | —OH | —Et | —OMe | 0.11 ± 0.01 | 48.1 ± 5.0 | 437 |
| LM5750A 8b | —OH | —Et | —OMe | 0.12 ± 0.01 | 1.72 ± 0.37 | 14 |
| DimethylNaproxen 9 | —OH | —diMe | —OMe | 0.27 | 1.32 | 5 |
| DesmethylNaproxen 10 | —OH | —H | —OMe | 0.65 ± 0.11 | 19.04 ± 3.7 | 29 |

As naproxen 1 is an S-enantiomer, its R-enantiomer, 1a was evaluated for AKR1C3 inhibition and selectivity. R-naproxen inhibited AKR1C3 and AKR1C2 with IC$_{50}$ values of 50 nM and 2.75 µM, respectively, which made it more potent and more selective for AKR1C3 than naproxen.

Replacement of the 6-OMe group of naproxen with an -Et to give 2, or an —OEt to give 3, did not change the potency and selectivity for AKR1C3. On the other hand, an isosteric replacement of the 6-OMe with the thiomethyl group —SMe to give compound 4, led to a 3-fold increase in the inhibitory potency for AKR1C3 (IC$_{50}$=60 nM) over that seen with naproxen, while the AKR1C2 inhibitory potency remained unchanged. This translated to 25-fold selectivity for AKR1C3 over AKR1C2 by compound 4. Because the —SMe group can be metabolized to the S(=O)Me and S(=O)$_2$Me groups, compounds 5 and 6 containing these functional groups at the 6-position were synthesized and screened for AKR1C3 activity and selectivity. Compared to 4, both compounds 5 and 6 displayed a greater than 15-fold loss of inhibitory potency on AKR1C3.

The N-(methylsulfonyl)acetamide analogue 7 displayed a significant loss of inhibitory activity for AKR1C3 and AKR1C2 with IC$_{50}$ values of 6.0 µM and 34 µM, respectively underscoring the need for a free carboxylic acid group for optimal inhibition of the AKR1C enzymes. Next, the replacement of the α-Me group of naproxen with an -Et gave 8, which was the most AKR1C3 selective racemate evaluated. With an IC$_{50}$ value of 120 nM against AKR1C3, compound 8 was significantly more potent as an AKR1C3 inhibitor than naproxen and was 58-fold selective for AKR1C3 over AKR1C2. Due to its favorable properties the racemic mixture of 8 was separated to give the R-(8a) and the S-(8b) enantiomers. The configuration of the enantiomers was inferred by comparing the elution order of the enantiomers with that of naproxen and R-naproxen when the same chiral column and mobile phase was used. Surprisingly, while the AKR1C3 inhibitory potency of the enantiomers was similar and not significantly different from the inhibitory potency of the racemate, the AKR1C2 inhibitory potency of the enantiomers was markedly different. The S-enantiomer inhibited AKR1C2 with an IC$_{50}$ of 1.72 µM, while the R-enantiomer displayed an IC$_{50}$ value of 46.4 µM against AKR1C2. This translated to 14- and 437-fold selectivity for AKR1C3 inhibition over AKR1C2, respectively. Eliminating the chiral center of naproxen by the introduction of α-diMe group to give 9 or by the removal of the α-Me group to give 10, led to a loss of inhibitory potency and selectivity for AKR1C3 indicating the importance in retaining the R-configuration.

The R- and S-enantiomers of compound 4 were also examined based on the selectivity achieved with the R-enantiomer 8a. Compound 4a showed 87-fold selectivity for AKR1C3, which was 5-fold less than the selectivity observed with compound 8a, demonstrating that the —OMe was preferred over the more bulky —SMe.

Compound 8a was the most selective AKR1C3 inhibitor identified from the primary screen. When tested for inhibition of AKR1C1, it displayed selectivity for AKR1C3 over AKR1C1 inhibiting the latter with an $IC_{50}$ value of 50 µM which translates to a 500 fold selectivity for AKR1C3 (FIG. 1).

Example 2: Effect of 8a on AKR1C2 Catalyzed Reduction of 5α-DHT

Figure 2:
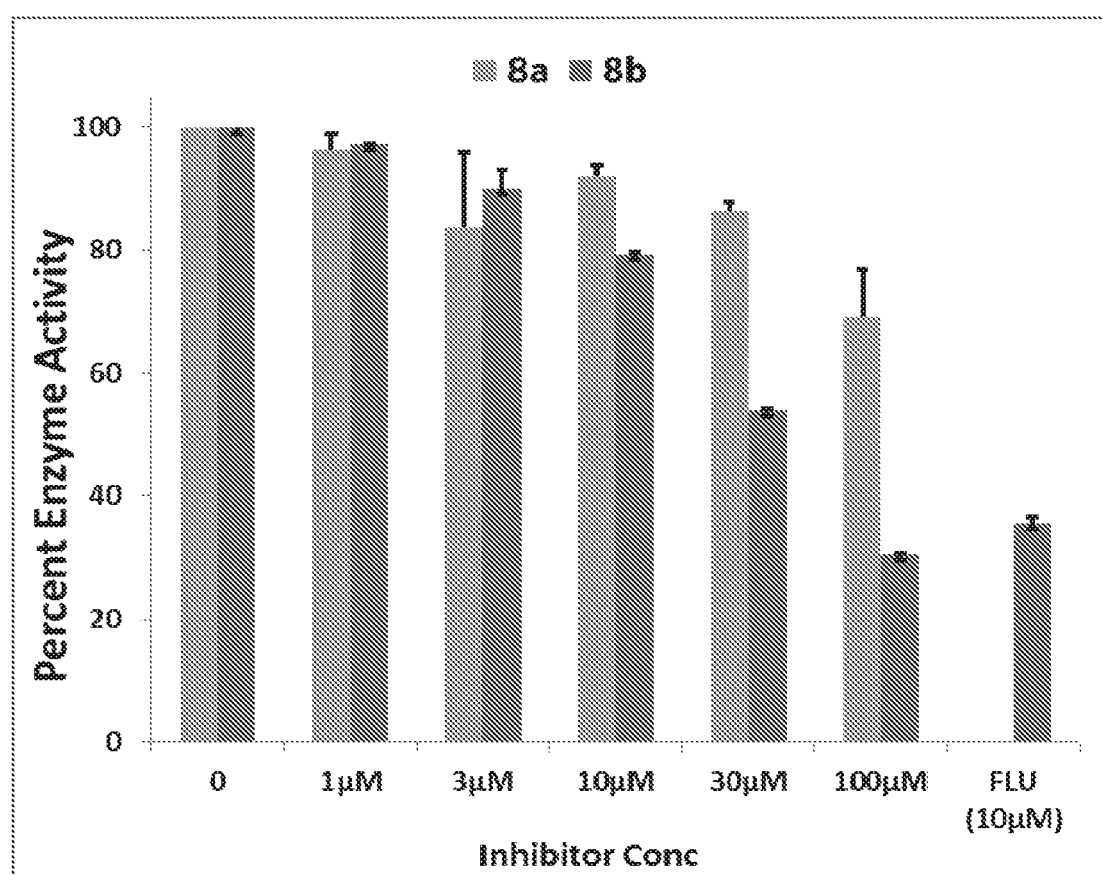
FIG. 2 is a bar graph illustrating the effect of compounds 8a (left bar) and 8b (right bar) on AKR1C2-catalyzed reduction of 5α-DHT.

Compound 8a and 8b were next evaluated for the ability to inhibit AKR1C2 catalyzed NADPH dependent reduction of 5α-DHT (AKR1C2's physiologically relevant steroidal substrate). In this reaction, compound 8b inhibited AKR1C2 in a dose dependent manner over the concentration range of 3-100 µM achieving 70% inhibition of enzyme activity at 100 µM (FIG. 2). In contrast, 8a did not display any significant inhibition of AKR1C2 at <100 µM concentrations. Flufenamic acid (FLU), a non-selective inhibitor of the AKR1C enzymes, displayed about 70% inhibition of AKR1C2 at 10 µM concentration.

Example 3: Mode of AKR1C3 Inhibition by 8a

Figure 3A:
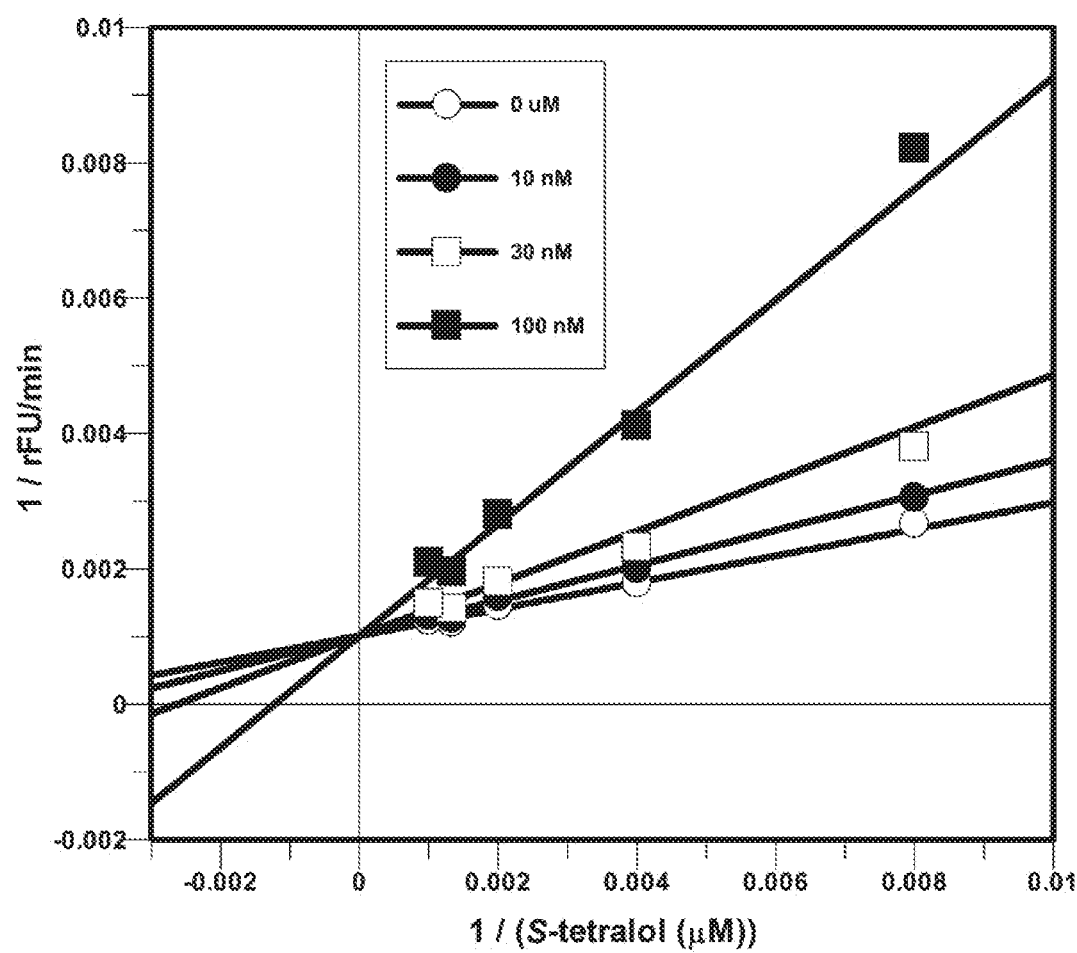
Figure 3B:
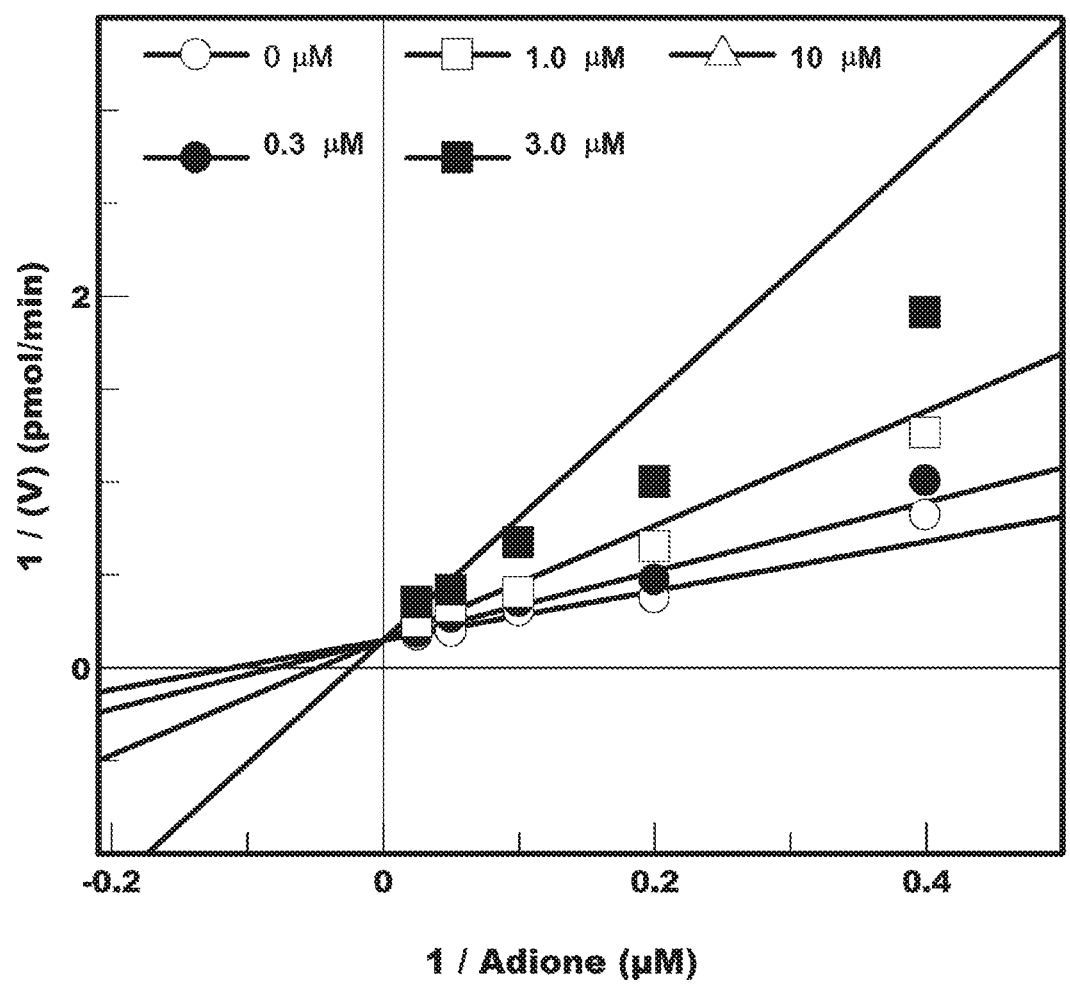

The pattern of AKR1C3 inhibition by 8a was evaluated by measuring the $NADP^+$ dependent oxidation of S-tetralol and by measuring the NADPH dependent reduction of $\Delta^4$-androsten-3,17-dione. Compound 8a competitively inhibited the AKR1C3 catalyzed oxidation of S-tetralol with a $K_i$ value of 31 nM (FIG. 3A). The same mode of inhibition was also observed when the reduction of $\Delta^4$-AD was monitored, albeit with a much higher $K_i$ value of 750 nM (FIG. 3B).

Example 4: Inhibition of COX-1

Naproxen inhibited COX-1 with an $IC_{50}$ value of 61 nM. Relative to naproxen, 8b displayed a 30-fold loss of inhibitory potency on COX-1 with an $IC_{50}$ value of 1.93 µM (FIG. 4). There was a profound loss of inhibitory activity on COX-1 activity by the respective R-enantiomers, compounds 1a and 8a. Both compounds displayed less than 20% inhibition of COX-1 activity at the highest inhibitor concentration (100 µM) tested. This is consistent with reported structure activity relationship studies on the COX-1 inhibitory effects of naproxen and its analogs.

A comparison of inhibitory potency of the compounds against AKR1C3 and COX-1 (Table 2) shows that 8a was almost a thousand fold more selective for AKR1C3 over COX-1. Compound 8, which is a racemate of 8a and 8b, had no inhibitory activity on COX-2 at the maximum concentration of arachidonic acid tested as substrate (10 µM).

TABLE 2

Inhibitory potency of compounds on AKR1C3 and COX-1

| Compound | AKR1C3 $IC_{50}$ (µM) | COX-1 $IC_{50}$ (µM) | COX-2 $IC_{50}$ (µM) | Ratio (COX-1 $IC_{50}$/ AKR1C3 $IC_{50}$) | Ratio (COX-2 $IC_{50}$/ AKR1C3 $IC_{50}$) |
|---|---|---|---|---|---|
| Naproxen 1a | 0.18 | 0.061 | 0.90 | 0.34 | 15 |
| R-naproxen (9) | 0.05 | >100 | >25 | >2000 | >500 |
| 8a | 0.11 | >100 | No inhibition | >910 | infinite |
| 8b | 0.12 | 1.93 | No inhibition | 16 | infinite |

Example 5: Effect on AR Reporter Gene Assay

Figure 5:
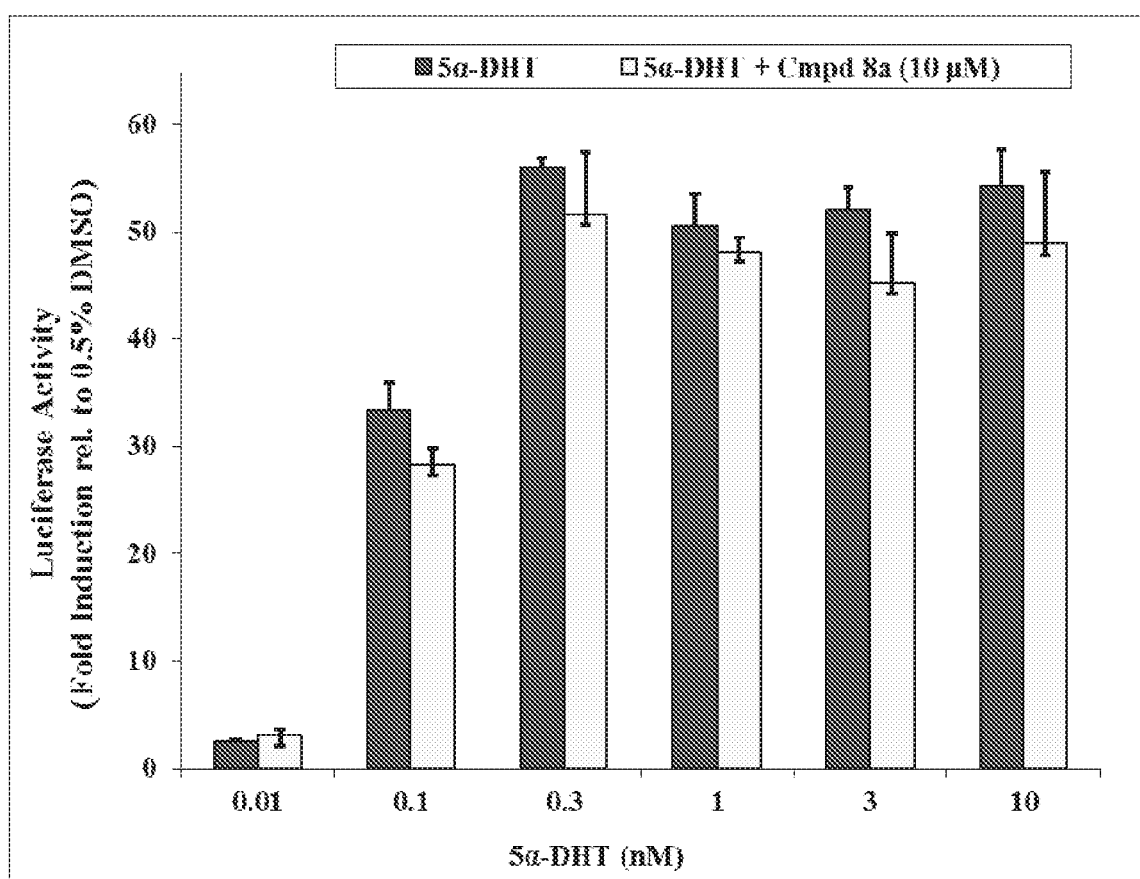
FIG. 5 is a bar graph illustrating the effect of compound 8a on DHT-induced AR gene expression. DHT alone (left bar) and DHT plus 10 μM compound 8a (right bar).

Compound 8a was next evaluated for a direct effect on AR signaling. Compound 8a did not affect the trans-activation of the AR mediated by 5α-DHT. There was a concentration-dependent increase in luciferase activity when HeLa13 cells containing a stably transfected AR and an androgen response element driven luciferase gene were treated with increasing concentrations of 5α-DHT. The luciferase activity peaked at 0.3 nM 5α-DHT, however, there were no significant change in the 5α-DHT induced luciferase expression when cells were treated with increasing concentrations of 5α-DHT in the presence of 10 µM compound 8a, FIG. 5.

Example 6: Inhibition of AKR1C3-Mediated Production of Testosterone

Figure 6A:
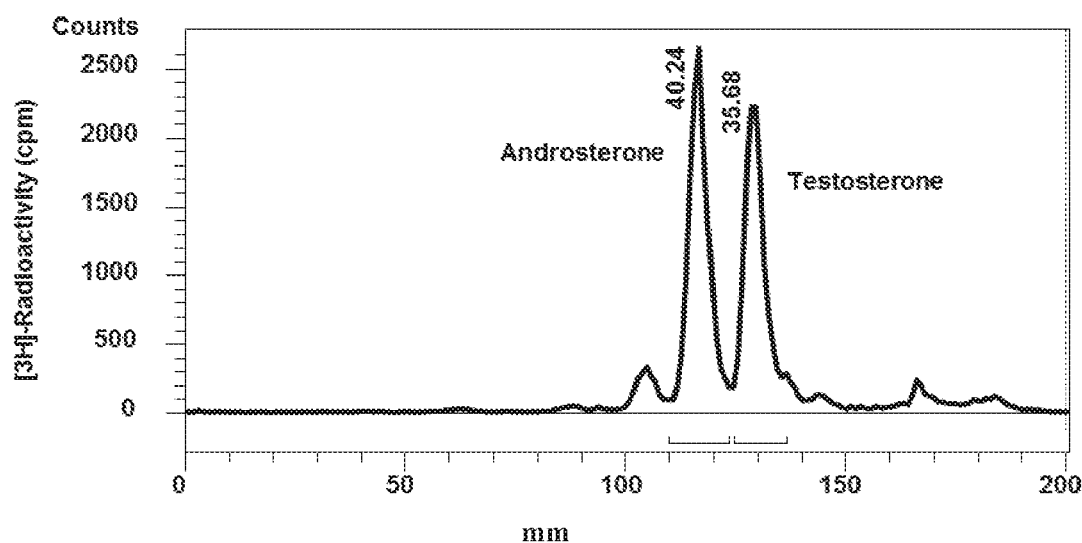
Figure 6B:
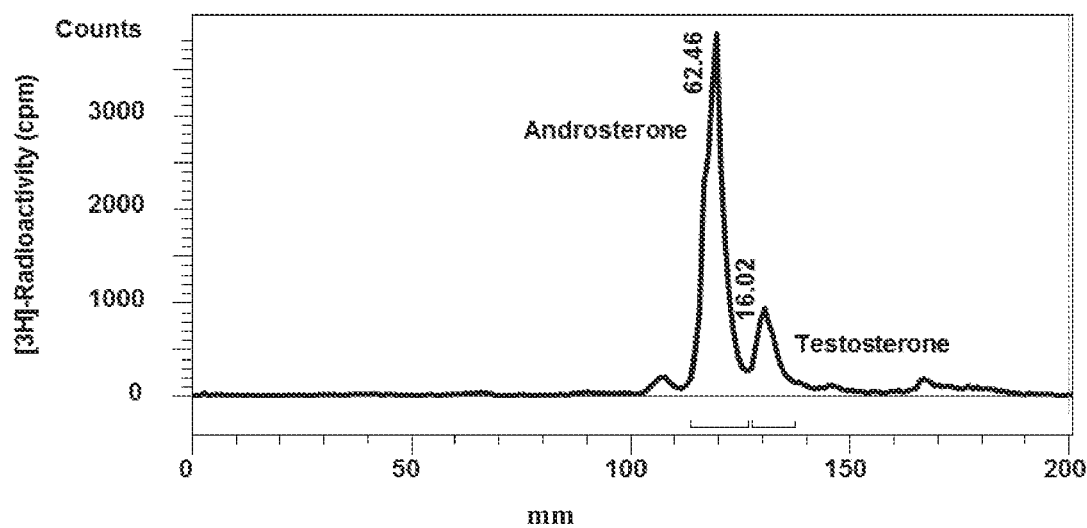
Figure 6C:
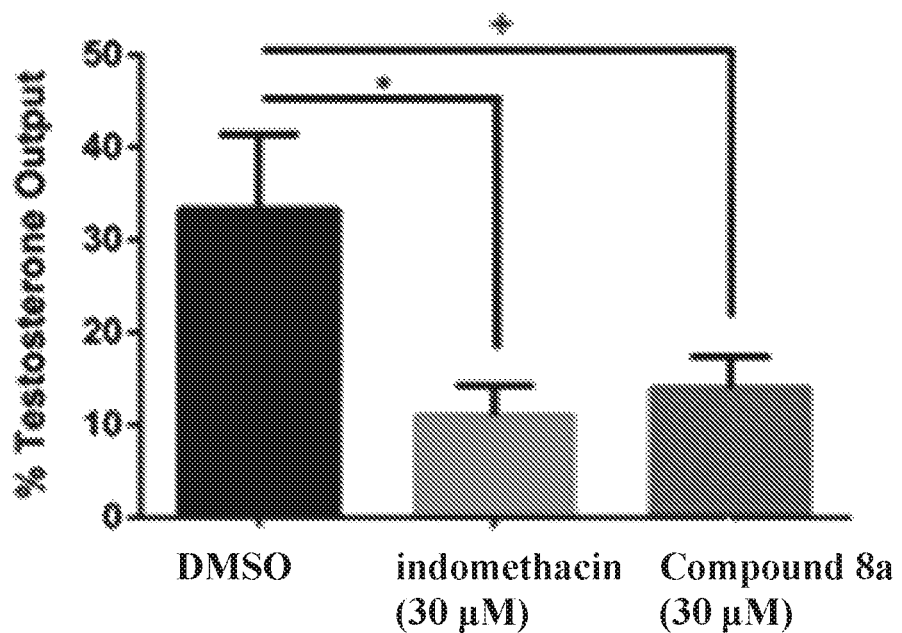
FIG. 6C comprises a bar graph illustrating statistical analysis (n=3) versus indomethacin as a positive control (*p value<0.001; p value=0.001).

LNCaP-AKR1C3 cells were used to probe the metabolism of $\Delta^4$-AD in the presence and absence of compound 8a. Radio-labeled $[^3H]$-$\Delta^4$-AD was incubated with carrier $\Delta^4$-AD (100 nM) with LNCaP-AKR1C3 cells placed in medium supplemented with charcoal dextran stripped fetal bovine serum (CD-FBS) which is devoid of androgens. Androgens were extracted after 48 hrs and the aqueous fraction subject to β-glucuronidase treatment to liberate androgen conjugates that we have previously shown to exist due to the robust uridine-5′-diphospho-glucuronosyltransferse (UGT) activity in these cells. Metabolites were separated by radiochromatography using TLC. LNCaP-AKR1C3 cells were able to metabolize $[^3H]$-$\Delta^4$-AD to $[^3H]$-androsterone glucuronide and $[^3H]$-testosterone glucuronide. However, in cells that were treated with 30 µM of compound 8a, the production of $^3H$-testosterone glucuronide was significantly inhibited (FIGS. 6A-6B).

Example 7: Inhibition of AKR1C3 Mediated AR Gene Expression

Figure 7A:
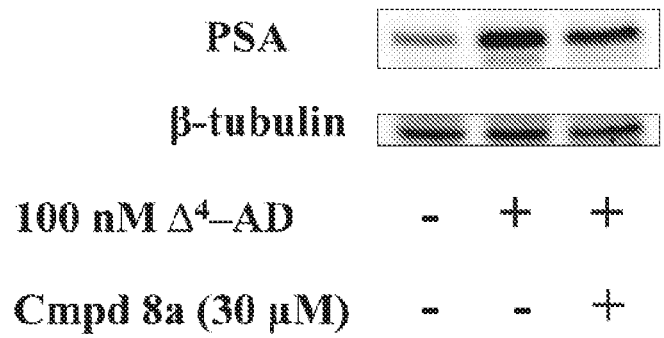
FIG. 7A is a set of images illustrating inhibition of $\Delta^4$-AD induced PSA expression in LNCaP-AKR1C3 cells.
Figure 7B:
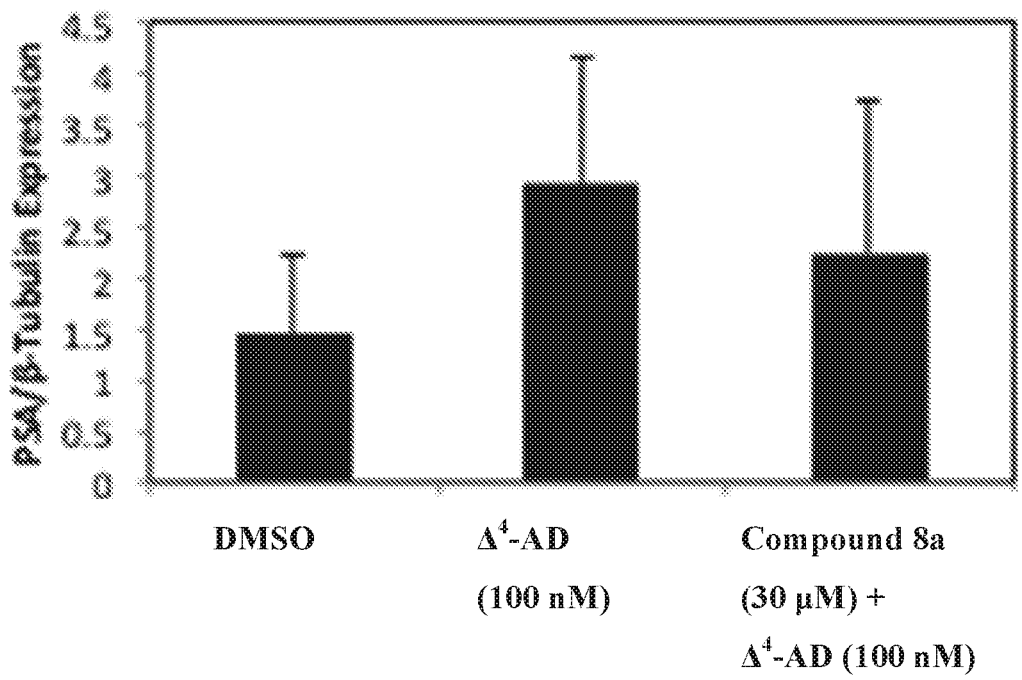
FIG. 7B is a bar graph illustrating densitometric traces of immunoblots with normalization of PSA to β-tubulin for biological replicates (n=3).

Compound 8a was also tested for its ability to block the $\Delta^4$-AD mediated expression of PSA in LNCaP-AKR1C3 cells by western blot analysis (FIG. 7A). Treatment of these cells with 100 nM $\Delta^4$-AD led to a robust increase in PSA expression. This increase in PSA was inhibited when the cells were treated with 100 nM $\Delta^4$-AD in the presence of 30 µM of compound 8a.

Example 8: Synthesis (S)-Methyl 2-(6-(trifluoromethylsulfonyloxy)naphthalen-2-yl)propanoate (D)

To (S)-naproxen (1, 3 g, 13 mmol) in acetic acid (20 mL) was added 48% HBr (11.2 g, 7.5 mL, 138 mmol) at 0° C.

Following 3 h of reflux, water (40 mL) was added to precipitate out the product B, which was isolated by filtration. To the crude product B was added methanol (35 mL) and TMSCl (1.7 g, 2.0 mL, 15.7 mmol), and the mixture was stirred at room temperature for 2 h. The solvent was removed in vacuum, resulting in a tan solid C, which was dissolved in $CH_2Cl_2$ (20 mL). Following the addition of triethylamine (2.6 g, 3.6 mL, 26.1 mmol) at 0° C., trifluoromethanesulfonic anhydride (2.8 g, 2.7 mL, 15.7 mmol) was added dropwise and the mixture was warmed to room temperature and allowed to stir for 1 h. The mixture was then diluted with diethyl ether, quenched with 1 M HCl, and washed with saturated sodium bicarbonate and brine. The organic layer was dried over $MgSO_4$ and then concentrated, resulting in the desired product D (4.5 g, 95%). $^1$H NMR (400 MHz, $CDCl_3$) δ 1.57 (d, 3H), 3.65 (s, 3H), 3.89 (q, 1H), 7.34 (dd, J=4, 8 Hz, 1H), 7.52 (dd, J=4, 8 Hz, 1H), 7.70 (d, J=4 Hz, 1H), 7.77 (s, 1H), 7.81 (d, J=8 Hz, 1H), 7.86 (d, J=8 Hz, 1H). MS m/z: 363 (M+H)$^+$.

2-(6-Ethylnaphthalen-2-yl)propanoic Acid (E)

(S)-Methyl 2-(6-(trifluoromethylsulfonyloxy)naphthalen-2-yl)propyl ester D (4.2 g, 11.6 mmol) and 1 M of cesium carbonate (20 mL) were added to a solution of potassium vinyltrifluoroborate (2.4 g, 17.5 mmol) in EtOH (100 mL). Then tetrakis (triphenylphosphine) palladium (672 mg, 0.59 mmol) and triethylamine (2.4 g, 3.2 mL, 23.8 mmol) were added to the mixture and stirred 50° C. for 16 h. The reaction mixture was cooled to room temperature, water (100 mL) was added, and the resulting mixture was stirred at room temperature for 30 min. The reaction mixture was filtered, resulting in (S)-methyl 2-(6-vinylnaphthalen-2-yl)propanoate as a brown solid (2 g), which was used directly to the next step without further purification. To a round-bottom flask purged with argon was added THF (35 mL), palladium (II) acetate (52 mg, 0.24 mmol), and tri-tert-butyl phosphine (94 mg, 113 mL, 0.46 mmol). This was brought to reflux and allowed to stir for 30 min. The reaction was then cooled, and (S)-methyl 2-(6-vinyl naphthalen-2-yl)propanoate (2 g, 8.9 mmol) and formic acid (2.7 g, 2.3 mL, 59 mmol) were added to the reaction mixture. The mixture was again brought to reflux for 30 min, then cooled to room temperature and allowed to stir for 12 h. The reaction mixture was filtered through a bed of Celite and then concentrated in vacuum to give the crude (S)-methyl 2-(6-ethylnaphthalen-2-yl)propanoate (700 mg), which was added to 14 mL of a 3 M KOH solution in MeOH. The reaction was held at reflux for 3 h, then cooled and quenched with water. The reaction mixture was extracted with ethyl ether (3×). The aqueous layer was then acidified with 1 M HCl and then extracted into ethyl ether (3×), washed with brine, dried with $MgSO_4$, and concentrated under reduced pressure to give a crude residue, which was purified by column chromatography (n-Hex:EtOAc 4:1) to afford the pure racemic product E (450 mg, yield 94% last step, purity 99.4%, HPLC retention time 11.93 min, melting point 120-122° C.). $^1$H NMR (600 MHz, DMSO-$d_6$) 1.18 (t, J=5.5 Hz, 3H), 1.38 (d, J=6 Hz, 3H), 2.68 (q, J=4.5 Hz, 2H), 3.75 (q, J=4.5 Hz, 1H), 7.30 (dd, J=7.5, 2.5 Hz, 1H), 7.34 (dd, J=7.5, 2.5 Hz, 1H), 7.58 (s, 1H), 7.66 (s, 1H), 7.71-7.73 (m, 2H). $^{13}$C NMR (150.9 MHz, DMSO-$d_6$) 15.98, 18.90, 28.75, 45.19, 125.47, 125.94, 126.43, 127.74, 127.92, 128.03, 131.98, 132.70, 138.41, 141.66, 175.86. HRMS: m/z calcd for $C_{15}H_{16}O_2$ (M−H)$^-$ 227.1078, found 227.1079.

2-(6-Ethoxynaphthalen-2-yl)propanoic Acid (F)

Potassium hydroxide (828 mg, 14.8 mmol) in 4 mL of methanol was added to a round-bottom flask. (S)-Methyl 2-(6-hydroxynaphthalen-2-yl)propyl methyl ester C (2.3 g, 9.8 mmol) in DMF (25 mL) was then added to the flask. The reaction was then allowed to stir at room temperature for 30 min. Iodoethane (3.0 g, 1.5 mL, 19.6 mmol) was added, which was allowed to stir at room temperature for 3 h. The reaction mixture was quenched with water and extracted with $CH_2Cl_2$ (3×), and the organic layer was then dried over $MgSO_4$, filtered, and finally concentrated in vacuum the crude product as a yellow solid (450 g), to which was added 8 mL of a 3 M KOH solution in MeOH. The reaction was held at reflux for 2 h, then cooled and quenched with water. The reaction mixture was extracted with ethyl ether (3×). The aqueous layer was then acidified with 1 M HCl and then extracted into ethyl ether (3×), washed with brine, dried with $MgSO_4$, and concentrated under reduced pressure to give pure racemic product as an off-white solid F (360 mg, yield 85% last step, purity 98%, HPLC retention time 11.28 min, melting point 148-150° C.). $^1$H NMR (600 MHz, DMSO-$d_6$) 1.44 (t, J=6 Hz, 3H), 1.49 (d, J=6.5 Hz, 3H), 3.85 (q, J=4.5 Hz, 1H), 4.19 (q, J=4.5 Hz, 1H), 7.20 (dd, J=2, 8.5 Hz, 1H), 7.32 (d, J=2 Hz, 1H), 7.44 (dd, J=2, 8.5 Hz, 1H), 7.76 (s, 1H), 7.78 (d, J=8.5, 1H), 7.85 (d, J=8.5, 1H). $^{13}$C NMR (150.9 MHz, DMSO-$d_6$) 15.10, 18.92, 45.06, 63.54, 106.83, 119.37, 126.00, 126.83, 127.28, 128.80, 129.56, 133.73, 136.74, 156.79, 175.95. HRMS: m/z calcd for $C_{15}H_{16}O_3$ (M−H)$^-$ 243.1027, found 243.1026.

(S)-Methyl 2-(6-(Triisopropylsilylthio)naphthalen-2-yl)-propanoate (G)

To a solution of (S)-methyl 2-(6-(trifluoromethylsulfonyloxy)naphthalen-2-yl)propyl methyl ester D (3 g, 8.3 mmol) in benzene (20 mL) was added Pd(PPh$_3$)$_4$ (0.95 g, 0.8 mmol) and sodium triisopropylsilanethiolate 60 (2.1 g, 9.9 mmol) dissolved in THF (10 mL). The solution was refluxed for 4 h, quenched with water and extracted with ethyl acetate. The organic layer was dried over $MgSO_4$ and concentrated. The crude product was purified by flash chromatography using 10:1 hexane:ethyl acetate to give pure product (2.9 g, 87%). $^1$H NMR (400 MHz, $CDCl_3$) δ 1.10 (d, 18H), 1.25 (m, 3H), 3.65 (s, 3H), 3.86 (q, 1H), 7.31 (m, 2H), 7.41 (dd, J=4, 8 Hz, 1H), 7.54 (dd, J=4, 8 Hz, 1H), 7.67 (m, 2H). MS m/z: 403 (M+H)$^+$.

(S)-Methyl 2-(6-(Methylthio)naphthalen-2-yl)propanoate (H)

To 15 mL of THF was added (S)-methyl 2-(6-(triisopropylsilylthio)-naphthalen-2-yl)propanoate 7 (2.5 g, 6.2 mmol) followed by tetrabutylammonium fluoride (3.3 g, 3.6 mL, 12.4 mmol). The mixture was allowed to stir at room temperature for 2 h. Methyl iodide (2.6 g, 1.2 mL, 18.6 mmol) was then added, and the resulting mixture was stirred for an additional 2 h at room temperature. The reaction mixture was extracted with ethyl ether, dried over $MgSO_4$, and concentrated in vacuum. The crude product H was purified by flash chromatography using 7:1 hexane:ethyl acetate to give pure product (1.2 g, 75%). $^1$H NMR (400 MHz, $CDCl_3$) δ 1.58 (d, 3H), 2.57 (s, 3H), 3.67 (s, 3H), 3.87 (q, 1H), 7.37 (dd, J=4, 8 Hz, 1H), 7.42 (dd, J=4, 8 Hz, 1H), 7.58 (s, 1H), 7.67 (s, 2H), 7.70 (d, J=8 Hz, 1H). MS m/z: 261 (M+H)$^-$.

2-(6-(Methylthio)naphthalen-2-yl)propanoic Acid (I)

To (S)-methyl 2-(6-(methylthio)naphthalen-2-yl)propanoate 8 (975 mg, 3.7 mmol) was added 20 mL of a 3 M KOH solution in MeOH. The reaction was refluxed for 2 h, cooled, and then quenched with water. Following extraction with ethyl ether, the aqueous layer was acidified with 1 M HCl and then extracted into ethyl ether, washed with brine, dried with $MgSO_4$, and concentrated under reduced pressure to give pure product I (876 mg, yield 95%, purity 99.1%, HPLC retention time 11.39 min, melting point 172-174° C.). $^1$H NMR (600 MHz, DMSO-$d_6$) δ 1.45 (d, J=6.5 Hz, 3H), 2.57 (s, 3H), 3.82 (q, J=5 Hz, 1H), 7.38 (dd, J=2, 8.5 Hz, 1H), 7.45 (dd, J=2, 8.5 Hz, 1H), 7.68 (s, 1H), 7.74 (s, 1H), 7.79-7.82 (m, 2H). $^{13}$C NMR (150.9 MHz, DMSO-$d_6$) 15.12, 18.85, 45.18, 63.54, 122.67, 125.84, 127.19, 127.32, 128.47, 131.14, 133.02, 136.13, 138.55, 175.79. HRMS: m/z calcd for $C_{14}H_{14}O_2S$ (M−H)$^-$ 245.0642, found 245.0637.

2-(6-(Methylsulfinyl)naphthalen-2-yl)propanoic Acid (J)

2-(6-(Methylthio)naphthalen-2-yl)propanoic acid 1 (65 mg, 0.26 mmol) was dissolved in 8 mL of dichloromethane. To this solution was added m-chloroperoxybenzoic acid (64 mg, 0.29 mmol), which was allowed to stir at 0° C. for 1 h. The reaction mixture was extracted with ethyl ether, dried over $MgSO_4$, and concentrated in vacuum. The crude product was purified by flash chromatography using 10:1 dichloromethane:methanol to give pure racemic product J (46 mg, yield 62%, purity 98.6%, HPLC retention time 7.16 min, melting point 130-132° C.). $^1$H NMR (600 MHz, DMSO-$d_6$) δ; 1.40 (d, J=6.5 Hz, 3H), 2.74 (s, 3H), 3.83 (q, J=5.5 Hz, 1H), 7.50 (dd. J=2.5, 8.5 Hz, 1H), 7.63 (dd, J=2, 8.5 Hz, 1H), 7.83 (s, 2H), 7.98 (dd, J=2.5, 8.5 Hz, 1H), 8.16 (s, 1H). $^{13}$C NMR (150.9 MHz, DMSO-$d_6$) 18.81, 43.50, 45.28, 120.83, 123.79, 126.45, 127.86, 127.86, 129.29, 131.10, 133.11, 141.20, 143.96, 175.59. HRMS: m/z calcd for $C_{14}H_{14}O_3S$ (M+H)$^+$ 263.0736, found 263.0741.

2-(6-(Methylsulfonyl)naphthalen-2-yl)propanoic Acid (K)

2-(6-(Methylthio)naphthalen-2-yl)propanoic acid 1 (82.5 mg, 0.33 mmol) was dissolved in 10 mL of acetone:water (2:1). To this solution was added Oxone (445.5 mg, 0.73 mmol), which was allowed to stir at room temperature for 2 h. The reaction mixture was extracted with ethyl ether (3×), dried over $MgSO_4$, and concentrated in vacuum to give pure racemic product K (56 mg, yield 60%, purity 97.8%, HPLC retention time 8.78 min, melting point 180-182° C.). $^1$H NMR (600 MHz, DMSO-$d_6$) δ 1.45 (d, J=6 Hz, 1H), 3.24 (s, 3H), 3.92 (q, J=5.5 Hz, 1H), 7.61 (dd, J=2.5, 8.5 Hz, 1H), 7.91 (dd, J=2.5, 8.5 Hz, 1H), 7.94 (s, 1H), 8.13-8.14 (m, 2H), 8.51 (s, 1H). $^{13}$C NMR (150.9 MHz, DMSO-$d_6$) 18.75, 44.05, 45.37, 122.93, 126.40, 128.34, 128.41, 129.78, 130.04, 131.16, 135.26, 138.16, 142.89, 175.44. HRMS: m/z calcd for $C_{14}H_{14}O_4S$ (M+H)$^+$ 279.0686, found 279.0926.

2-(6-Methoxynaphthalen-2-yl)butanoic Acid (N)

To a flask charged with 18 mL of THF and purged with argon was added magnesium ribbon (435.6 mg, 18 mmol) and a crystal of iodine. To this solution was added 2-bromo-6-methoxynaphthalene 12 (3.6 g, 15 mmol) in 18 mL of THF. An off-brown color appeared, and the reaction was allowed to reflux for 1 h. The reaction was then allowed to cool, and methyl 2-bromobutyrate (5.4 g, 3.4 mL, 30.2 mmol) was added. Following 2 h of reflux, the reaction was quenched with 1 M HCl, then extracted with ethyl ether (3×), washed with brine, dried with $MgSO_4$, and concentrated under reduced pressure. The crude mixture was suspended in 18 mL of a 3 M KOH solution in MeOH, held at reflux for 2 h, cooled, and then quenched with water. The reaction mixture was extracted with ethyl ether (3×). The aqueous layer was then acidified with 1 M HCl, extracted into ethyl ether (3×), washed with brine, dried with $MgSO_4$, and concentrated under reduced pressure to give crude racemic product N. The product was purified using HPLC on a C18 column (2 g, yield 55%, purity 99.8%, HPLC retention time 15.8 min, melting point 115-117° C.) to give pure racemic product. $^1$H NMR (600 MHz, DMSO-$d_6$) δ 0.84 (t, J=7 Hz, 3H), 1.74-1.77 (m, 1H), 2.02-2.06 (m, 1H), 3.52 (t, J=5.5 Hz, 1H), 3.86 (s, 3H), 7.11 (dd, J=2.5, 8.7 Hz, 1H), 7.28 (d, J=2.5 Hz, 1H), 7.40 (dd, J=2.5, 8.7 Hz, 1H), 7.71 (s, 1H), 7.76-7.80 (m, 2H). $^{13}$C NMR (150.9 MHz, DMSO-$d_6$) 12.56, 26.50, 53.01, 55.63, 106.17, 119.16, 126.69, 126.99, 127.31, 128.86, 129.57, 133.78, 135.24, 157.56, 175.40. HRMS: m/z calcd for $C_{15}H_{16}O_3$ (M−H)$^-$ 243.1027. found 243.1024.

2-(6-Methoxynaphthalen-2-yl)-N-(methylsulfonyl)butanamide (O)

To an ice-cold mixture (0-5° C.) of 2-(6-methoxynaphthalen-2-yl)butanoic acid N (87 mg, 0.39 mmol) in dry $CH_2Cl_2$ (3 mL) under argon was added 1,1'-carbonyldiimidazole (63 mg, 0.39 mmol). After the reaction mixture was stirred for 2 h at 0-5° C., methanesulfonamide (33 mg, 0.39 mmol) and diazabicyclo[5.4.0]-undec-7-ene (59 mg, 0.39 mmol) (1 equiv) were added. The mixture was left stirring for another 4 h at ambient temperature before it was quenched by the addition of glacial acetic acid (52 μL) and diluted with additional $CH_2Cl_2$ (1 mL). The organic layer was separated and washed with 10% $NaH_2PO_4$ buffer (pH 4) (2×3 mL) and water (3×3 mL), dried over $Na_2SO_4$, filtered, and concentrated under reduced pressure to give a crude residue. The raw product was purified by flash chromatography ($SiO_2$, ethyl acetate/hexane gradient) to afford the product (52 mg, yield 45%, purity 98.5%, HPLC retention time 11.20 min, melting point 144-146° C.) of the pure title compound. $^1$H NMR (600 MHz, DMSO-$d_6$) δ 0.82 (t, J=7.46 Hz, 3H), 1.73-1.75 (m, 1H), 2.02-2.06 (m, 1H), 3.18 (s, 3H), 3.61 (t, J=7.04 Hz, 1H), 3.85 (s, 3H), 7.14 (dd, J=9.5, 2.1 Hz, 1H), 7.27 (d, J=2.2 Hz, 1H), 7.39 (dd, J=9.2, 2.0 Hz, 1H), 7.69 (s, 1H), 7.77 (d, J=9.7 Hz, 1H), 7.79 (d, J=9.8 Hz, 1H). $^{13}$C NMR (150.9 MHz, DMSO-$d_6$) 12.37, 26.37, 41.35, 53.35, 55.61, 106.14, 119.22, 126.78, 126.84, 127.38, 128.75, 129.62, 133.88, 134.24, 157.67, 173.72. HRMS: m/z calcd for $C_{16}H_{19}NO_{4S}$ (M−H)$^-$ 320.0962, found 320.0966.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A (R)-enantiomer compound of formula (Ia), or a salt or solvate thereof:

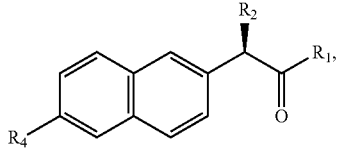

wherein:
R$_1$ is selected from the group consisting of OH, —NHSO$_2$(C$_1$-C$_6$ alkyl), C$_1$-C$_6$ alkoxy, and C$_3$-C$_8$ cycloalkoxy,
wherein the alkyl, alkoxy or cycloalkoxy group is optionally substituted with at least one substituent selected from C$_1$-C$_6$ alkyl, C$_3$-C$_8$ cycloalkyl, optionally substituted aryl, OH, C$_1$-C$_6$ alkoxy, halogen, and —CN;
R$_2$ is ethyl; and
R$_4$ is selected from the group consisting of C$_1$-C$_6$ alkyl, C$_3$-C$_8$ cycloalkyl, C$_1$-C$_6$ alkoxy, C$_3$-C$_8$ cycloalkoxy, —S(C$_1$-C$_6$ alkyl), —S(C$_3$-C$_8$ cycloalkyl), —S(=O)(C$_1$-C$_6$ alkyl), —S(=O)(C$_3$-C$_8$ cycloalkyl), —S(=O)$_2$(C$_1$-C$_6$ alkyl), and —S(=O)$_2$(C$_3$-C$_8$ cycloalkyl);
wherein the compound is free of the corresponding (S)-enantiomer.

2. The compound of claim 1, wherein R$_1$ is selected from the group consisting of OH and C$_1$-C$_6$ alkoxy, wherein the alkoxy group is optionally substituted with at least one substitutent selected from the group consisting of C$_1$-C$_6$ alkyl, optionally substituted aryl, OH, C$_1$-C$_6$ alkoxy, halogen, and —CN.

3. The compound of claim 1, wherein R$_1$ is OH, methoxy, ethoxy, i-propoxy, n-propoxy, n-butoxy, i-butoxy, sec-butoxy, or t-butoxy.

4. The compound of claim 1, wherein R4 is selected from the group consisting of C$_1$-C$_6$ alkyl, C$_1$-C$_6$ alkoxy, —S(C$_1$-C$_6$ alkyl), —S(=O)(C$_1$-C$_6$ alkyl), and —S(=O)$_2$(C$_1$-C$_6$ alkyl).

5. The compound of claim 1, wherein R$_4$ is methyl, methoxy, ethyl, ethoxy, —S(=O)CH$_3$, —S(=O)$_2$CH$_3$, —S(=O)CH$_2$CH$_3$, or —S(=O)$_2$CH$_2$CH$_3$.

6. A pharmaceutical composition comprising at least one compound of claim 1 and further comprising at least one pharmaceutically acceptable carrier.

7. The pharmaceutical composition of claim 6, further comprising at least one additional agent that treats or ameliorates cancer.

8. The compound selected from the group consisting of:
2(R)-(6-ethylnaphthalen-2-yl)propanoic acid;
2(R)-(6-ethoxynaphthalen-2-yl)propanoic acid;
2(R)-(6-(methylsulfinyl)naphthalen-2-yl)propanoic acid;
2(R)-(6-methoxynaphthalen-2-yl)-N-(methylsulfonyl)butanamide; and
2(R)-(6-methoxynaphthalen-2-yl)butanoic acid;
or a salt or solvate thereof, or any mixtures thereof;
wherein the compound is free of the corresponding (S)-enantiomer.

9. The compound 2(R)-(6-methoxynaphthalen-2-yl)butanoic acid

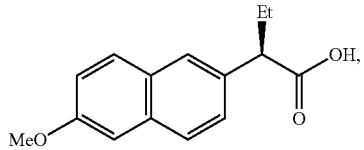

or a salt or solvate thereof, or any mixtures thereof;
wherein the compound is free of the corresponding (S)-enantiomer.

10. A method of treating or ameliorating prostate cancer in a subject in need thereof, the method comprising administering to the subject a therapeutically effective amount of at least one compound of formula (Ia), or a salt or solvate thereof:

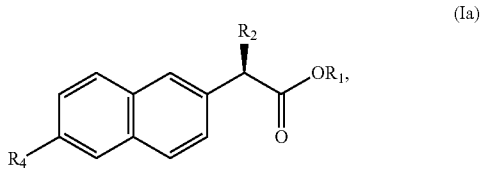

wherein:
R$_1$ is selected from the group consisting of OH, —NHSO$_2$(C$_1$-C$_6$ alkyl), C$_1$-C$_6$ alkoxy, and C$_3$-C$_8$ cycloalkoxy,
wherein the alkyl, alkoxy or cycloalkoxy group is optionally substituted with at least one substituent selected from C$_1$-C$_6$ alkyl, C$_3$-C$_8$ cycloalkyl, optionally substituted aryl, OH, C$_1$-C$_6$ alkoxy, halogen, and —CN;
R$_2$ is ethyl; and
R$_4$ is selected from the group consisting of C$_1$-C$_6$ alkyl, C$_3$-C$_8$ cycloalkyl, C$_1$-C$_6$ alkoxy, C$_3$-C$_8$ cycloalkoxy, —S(C$_1$-C$_6$ alkyl), —S(C$_3$-C$_8$ cycloalkyl), —S(=O)(C$_1$-C$_6$ alkyl), —S(=O)(C$_3$-C$_8$ cycloalkyl), —S(=O)$_2$(C$_1$-C$_6$ alkyl), and —S(=O)$_2$(C$_3$-C$_8$ cycloalkyl);
wherein the compound is free of the corresponding (S)-enantiomer.

11. The method of claim 10, wherein the cancer comprises castration-resistant prostate cancer.

12. The method of claim 10, the method further comprising administering to the subject at least one therapeutic agent selected from the group consisting of indomethacin, desatinib, selegiline, seliciclib, TOK-001, SAHA, docetaxel, bevacizumab, taxotere, thalidomide, prednisone, Sipuleucel-T, cabazitaxel, enzalutamide, ARN-509, abiraterone, temozolomide, any salt thereof, any solvates thereof, and any mixtures thereof.

13. The method of claim 10, wherein the compound promotes analgesia in the subject suffering from prostate cancer.

14. A method of inhibiting aldo-keto reductase family 1, member C3 (AKR1C3) in a mammalian cell, the method comprising contacting the cell with an effective amount of at least one compound of formula (Ia), or a salt or solvate thereof:

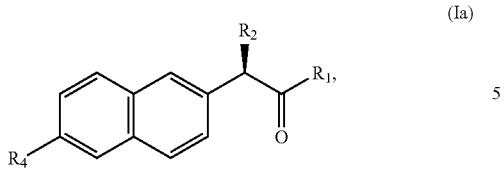

(Ia)

wherein:
R₁ is selected from the group consisting of OH, —NHSO₂(C₁-C₆ alkyl), C₁-C₆ alkoxy, and C₃-C₈ cycloalkoxy,
   wherein the alkyl, alkoxy or cycloalkoxy group is optionally substituted with at least one substituent selected from C₁-C₆ alkyl, C₃-C₈ cycloalkyl, optionally substituted aryl, OH, C₁-C₆ alkoxy, halogen, and —CN;

R₂ is ethyl; and

R₄ is selected from the group consisting of C₁-C₆ alkyl, C₃-C₈ cycloalkyl, C₁-C₆ alkoxy, C₃-C₈ cycloalkoxy, —S(C₁-C₆ alkyl), —S(C₃-C₈ cycloalkyl), —S(=O)(C₁-C₆ alkyl), —S(=O)(C₃-C₈ cycloalkyl), —S(=O)₂(C₁-C₆ alkyl), and —S(=O)₂(C₃-C₈ cycloalkyl);

wherein the compound is free of the corresponding (S)-enantiomer.

15. The method of claim 14, wherein the cell comprises a prostate cell.

16. The method of claim 15, wherein the cell comprises a prostate cancer cell or a castration-resistant prostate cancer cell.

17. The method of claim 14, wherein the cell is in vivo in the mammal.

* * * * *